(12) United States Patent
Foo et al.

(10) Patent No.: US 7,977,502 B2
(45) Date of Patent: Jul. 12, 2011

(54) PROCESS FOR MAKING AND REFINING 3-PENTENENITRILE, AND FOR REFINING 2-METHYL-3-BUTENENITRILE

(75) Inventors: Thomas Foo, Wilmington, DE (US); Sigridur S. Kristjansdottir, Wilmington, DE (US); Ronald J. McKinney, Wilmington, DE (US); Ron Ozer, Arden, DE (US); Paul S. Pearlman, Thornton, PA (US)

(73) Assignee: Invista North America S.A R.L., Wilmington, DE (US)

( * ) Notice: Subject to any disclaimer, the term of this patent is extended or adjusted under 35 U.S.C. 154(b) by 368 days.

(21) Appl. No.: 12/353,410

(22) Filed: Jan. 14, 2009

(65) Prior Publication Data

US 2009/0182163 A1    Jul. 16, 2009

Related U.S. Application Data

(60) Provisional application No. 61/021,217, filed on Jan. 15, 2008.

(51) Int. Cl.
*C07C 253/10* (2006.01)
(52) U.S. Cl. ...................................................... 558/338
(58) Field of Classification Search ........................ None
See application file for complete search history.

(56) References Cited

U.S. PATENT DOCUMENTS

| | | | |
|---|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard et al. |
| 3,551,474 A | 12/1970 | Drinkard et al. |
| 3,564,040 A | 2/1971 | Downing et al. |
| 3,579,560 A | 5/1971 | Drinkard et al. |
| 3,655,723 A | 4/1972 | Drinkard, Jr. et al. |
| 3,655,729 A | 4/1972 | Rinehart |
| 3,694,485 A | 9/1972 | Drinkard, Jr. et al. |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,853,754 A | 12/1974 | Gosser |
| 3,853,948 A | 12/1974 | Drinkard, Jr. et al. |
| 3,864,380 A | 2/1975 | King et al. |
| 3,869,501 A | 3/1975 | Waddan |
| 3,903,120 A | 9/1975 | Shook, Jr. et al. |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,328,172 A | 5/1982 | Rapoport |

(Continued)

FOREIGN PATENT DOCUMENTS

AU          6522096          2/1997

(Continued)

OTHER PUBLICATIONS

U.S. Appl. No. 08/379,429.

(Continued)

*Primary Examiner* — Kamal Saeed

(57) ABSTRACT

The invention provides an integrated, continuous process for the production of 3-pentenenitrile, the refining of 3-pentenenitrile, and the refining of 2-methyl-3-butenenitrile, the process comprising:

Figure 1:
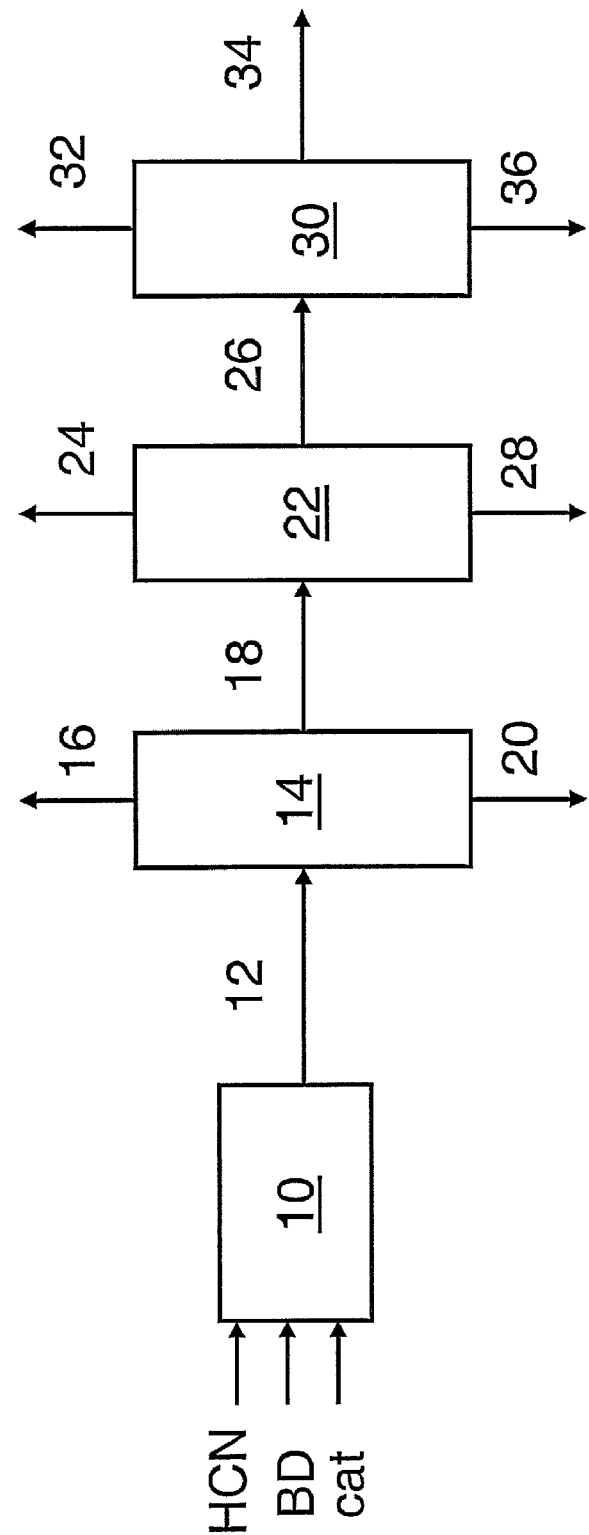

(a) contacting, in a reaction zone, a hydrogen cyanide-containing feed, a butadiene-containing feed, and a catalyst composition, wherein the catalyst composition comprises a zero-valent nickel and at least one bidentate phosphorus-containing ligand selected from the group consisting of a phosphite, a phosphonite, a phosphinite, a phosphine, a mixed phosphorus-containing ligand, and combination thereof;

(b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture;

(c) distilling the reaction mixture to obtain a first stream comprising 1,3-butadiene, a second stream comprising 3-pentenenitrile, 2-methyl-3-butenenitrile, (Z)-2-methyl-2-butenenitrile, and optionally 1,3-butadiene, and a third stream comprising the catalyst composition;

(d) distilling the second stream to obtain a fourth stream comprising 1,3-butadiene, a fifth stream comprising 2-methyl-3-butenenitrile, (Z)-2-methyl-2-butenenitrile, and optionally 1,3-butadiene, and a sixth stream comprising 3-pentenenitrile; and (e) distilling the fifth stream to obtain a seventh stream comprising 1,3-butadiene, an eighth stream comprising (Z)-2-methyl-2-butenenitrile, and a ninth stream comprising 2-methyl-3-butenenitrile.

23 Claims, 5 Drawing Sheets

U.S. PATENT DOCUMENTS

| | | |
|---|---|---|
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |
| 4,416,825 A | 11/1983 | Ostermaier |
| 4,434,316 A | 2/1984 | Barnette |
| 4,539,302 A | 9/1985 | Leyendecker et al. |
| 4,705,881 A | 11/1987 | Rapoport |
| 4,749,801 A | 6/1988 | Bealty et al. |
| 4,774,353 A | 9/1988 | Hall et al. |
| 4,874,884 A | 10/1989 | McKinney et al. |
| 4,990,645 A | 2/1991 | Back et al. |
| 5,107,012 A | 4/1992 | Grunewald |
| 5,302,756 A | 4/1994 | McKinney |
| 5,312,959 A | 5/1994 | Sieja et al. |
| 5,449,807 A | 9/1995 | Druliner |
| 5,488,129 A | 1/1996 | Huser et al. |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,693,843 A | 12/1997 | Breikss |
| 5,696,280 A | 12/1997 | Shapiro |
| 5,709,841 A | 1/1998 | Reimer |
| 5,723,641 A | 3/1998 | Tam et al. |
| 5,773,637 A | 6/1998 | Cicha et al. |
| 5,821,378 A | 10/1998 | Foo et al. |
| 5,847,191 A | 12/1998 | Bunel et al. |
| 5,856,555 A | 1/1999 | Huser et al. |
| 5,908,805 A | 6/1999 | Huser et al. |
| 5,959,135 A | 9/1999 | Garner et al. |
| 5,981,772 A | 11/1999 | Foo et al. |
| 6,020,516 A | 2/2000 | Foo et al. |
| 6,069,267 A | 5/2000 | Tam |
| 6,090,987 A | 7/2000 | Billig et al. |
| 6,121,184 A | 9/2000 | Druliner et al. |
| 6,127,567 A | 10/2000 | Garner et al. |
| 6,147,247 A | 11/2000 | Voit et al. |
| 6,169,198 B1 | 1/2001 | Fischer et al. |
| 6,171,996 B1 | 1/2001 | Garner et al. |
| 6,171,997 B1 | 1/2001 | Foo et al. |
| 6,197,992 B1 | 3/2001 | Fischer et al. |
| 6,242,633 B1 | 6/2001 | Fischer et al. |
| 6,284,865 B1 | 9/2001 | Tam et al. |
| 6,307,109 B1 | 10/2001 | Kanel et al. |
| 6,355,833 B2 | 3/2002 | Fischer et al. |
| 6,461,481 B1 | 10/2002 | Barnette et al. |
| 6,469,194 B2 | 10/2002 | Burattin et al. |
| 6,521,778 B1 | 2/2003 | Fischer et al. |
| 6,646,148 B1 | 11/2003 | Kreutzer |
| 6,660,877 B2 | 12/2003 | Lenges et al. |
| 6,737,539 B2 | 5/2004 | Lenges et al. |
| 6,753,440 B2 | 6/2004 | Druliner et al. |
| 6,770,770 B1 | 8/2004 | Baumann et al. |
| 6,846,945 B2 | 1/2005 | Lenges et al. |
| 6,852,199 B2 | 2/2005 | Jungkamp et al. |
| 6,855,799 B2 | 2/2005 | Tam et al. |
| 6,893,996 B2 | 5/2005 | Chu et al. |
| 6,897,329 B2 | 5/2005 | Jackson et al. |
| 6,924,345 B2 | 8/2005 | Gagne et al. |
| 6,936,171 B2 | 8/2005 | Jackson et al. |
| 6,984,604 B2 | 1/2006 | Cobb et al. |
| 7,022,866 B2 | 4/2006 | Bartsch et al. |
| 7,067,685 B2 | 6/2006 | Bartsch et al. |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,700,795 B2 | 4/2010 | Haderlein et al. |
| 2001/0014647 A1 | 8/2001 | Fischer et al. |
| 2001/0049431 A1 | 12/2001 | Tam et al. |
| 2003/0045740 A1 | 3/2003 | Druliner et al. |
| 2003/0100802 A1 | 5/2003 | Shapiro |
| 2003/0135014 A1 | 7/2003 | Radu et al. |
| 2003/0212298 A1 | 11/2003 | Brasse et al. |
| 2004/0012225 A1 | 1/2004 | Schlecht et al. |
| 2004/0063956 A1 | 4/2004 | Burattin et al. |
| 2004/0063991 A1 | 4/2004 | Burattin et al. |
| 2004/0106815 A1 | 6/2004 | Ritter |
| 2004/0176622 A1 | 9/2004 | Bartsch et al. |
| 2004/0235648 A1 | 11/2004 | Bartsch et al. |
| 2004/0260112 A1 | 12/2004 | Basset et al. |
| 2005/0090677 A1 | 4/2005 | Bartsch et al. |
| 2005/0090678 A1 | 4/2005 | Bartsch et al. |
| 2005/0247624 A1 | 11/2005 | Jungkamp et al. |
| 2006/0142609 A1 | 6/2006 | Bourgeois et al. |
| 2006/0175189 A1 | 8/2006 | Gerber et al. |
| 2006/0252955 A1 | 11/2006 | Rosier et al. |
| 2006/0258873 A1 | 11/2006 | Rosier et al. |
| 2006/0258874 A1 | 11/2006 | Bartsch et al. |
| 2006/0264651 A1 | 11/2006 | Bartsch et al. |
| 2007/0060766 A1 | 3/2007 | Bartsch et al. |
| 2007/0073071 A1 | 3/2007 | Haderlein et al. |
| 2007/0083057 A1 | 4/2007 | Haderlein et al. |
| 2007/0088173 A1 | 4/2007 | Haderlein et al. |
| 2007/0112215 A1 | 5/2007 | Jungkamp et al. |
| 2007/0155977 A1 | 7/2007 | Jungkamp et al. |
| 2007/0155978 A1 | 7/2007 | Jungkamp et al. |
| 2007/0155980 A1 | 7/2007 | Scheidel et al. |
| 2008/0015378 A1 | 1/2008 | Foo et al. |
| 2008/0015380 A1 | 1/2008 | Foo et al. |
| 2008/0015381 A1 | 1/2008 | Foo et al. |
| 2008/0015382 A1 | 1/2008 | Foo et al. |
| 2008/0071105 A1 | 3/2008 | Bartsch et al. |
| 2008/0076944 A1 | 3/2008 | Bartsch et al. |
| 2008/0083607 A1 | 4/2008 | Deckert et al. |
| 2008/0221351 A1 | 9/2008 | Bartsch et al. |
| 2008/0227214 A1 | 9/2008 | Jungkamp et al. |
| 2008/0227998 A1 | 9/2008 | Scheidel et al. |
| 2008/0242883 A1 | 10/2008 | Jungkamp et al. |
| 2008/0242885 A1 | 10/2008 | Jungkamp et al. |
| 2008/0242886 A1 | 10/2008 | Bartsch et al. |
| 2008/0275266 A1 | 11/2008 | Bartsch et al. |
| 2008/0281119 A1 | 11/2008 | Scheidel et al. |
| 2008/0281120 A1 | 11/2008 | Jungkamp et al. |
| 2009/0054671 A1 | 2/2009 | Haderlein et al. |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |

| | | | | | | | |
|---|---|---|---|---|---|---|---|
| CN | 1266424 | A | 9/2000 | CN | 101020641 | A | 8/2007 |
| CN | 1270543 | A | 10/2000 | CN | 101035799 | A | 9/2007 |
| CN | 1068307 | C | 7/2001 | CN | 101043946 | A | 9/2007 |
| CN | 1304334 | A | 7/2001 | CN | 100348322 | C | 11/2007 |
| CN | 1069310 | C | 8/2001 | CN | 100351227 | C | 11/2007 |
| CN | 1072980 | C | 10/2001 | CN | 100352824 | C | 12/2007 |
| CN | 1076342 | C | 12/2001 | CN | 100361966 | C | 1/2008 |
| CN | 1327881 | A | 12/2001 | CN | 100364666 | C | 1/2008 |
| CN | 1331843 | A | 1/2002 | DE | 1807088 | U | 3/1960 |
| CN | 1333745 | A | 1/2002 | DE | 1807088 | A1 | 6/1969 |
| CN | 1082946 | C | 4/2002 | DE | 2055747 | A1 | 5/1971 |
| CN | 1344180 | A | 4/2002 | DE | 1593277 | B2 | 8/1973 |
| CN | 1356335 | A | 7/2002 | DE | 1593277 | C3 | 3/1974 |
| CN | 1387534 | A | 12/2002 | DE | 2700904 | C2 | 10/1983 |
| CN | 1099912 | C | 1/2003 | DE | 68909466 | T2 | 3/1994 |
| CN | 1390241 | A | 1/2003 | DE | 10046025 | | 3/2002 |
| CN | 1103613 | C | 3/2003 | DE | 10136488 | A1 | 2/2003 |
| CN | 1106218 | C | 4/2003 | DE | 10150285 | A1 | 4/2003 |
| CN | 1108643 | C | 5/2003 | DE | 10350999 | A1 | 6/2005 |
| CN | 1427807 | A | 7/2003 | DE | 102004004696 | A1 | 8/2005 |
| CN | 1449400 | A | 10/2003 | EP | 0001899 | B1 | 3/1982 |
| CN | 1461295 | A | 12/2003 | EP | 123438 | B1 | 7/1987 |
| CN | 1471510 | A | 1/2004 | EP | 160296 | B1 | 10/1988 |
| CN | 1141285 | C | 3/2004 | EP | 268448 | B1 | 9/1991 |
| CN | 1142224 | C | 3/2004 | EP | 510689 | A1 | 10/1992 |
| CN | 1144781 | C | 4/2004 | EP | 248643 | B1 | 3/1993 |
| CN | 1487917 | A | 4/2004 | EP | 336314 | B1 | 9/1993 |
| CN | 1152855 | C | 6/2004 | EP | 464691 | B1 | 12/1993 |
| CN | 1535179 | A | 10/2004 | EP | 675871 | B1 | 4/1997 |
| CN | 1564807 | A | 1/2005 | EP | 634395 | B1 | 9/1997 |
| CN | 1568225 | A | 1/2005 | EP | 650959 | B1 | 9/1997 |
| CN | 1568226 | A | 1/2005 | EP | 784610 | B1 | 2/1999 |
| CN | 1617892 | A | 5/2005 | EP | 757672 | B1 | 6/1999 |
| CN | 1617900 | A | 5/2005 | EP | 792259 | B1 | 8/1999 |
| CN | 1212293 | C | 7/2005 | EP | 804412 | B1 | 12/1999 |
| CN | 1639176 | A | 7/2005 | EP | 1000019 | A1 | 5/2000 |
| CN | 1213051 | C | 8/2005 | EP | 1001928 | A1 | 5/2000 |
| CN | 1665776 | A | 9/2005 | EP | 1003716 | A1 | 5/2000 |
| CN | 1670139 | A | 9/2005 | EP | 1019190 | A1 | 7/2000 |
| CN | 1674989 | A | 9/2005 | EP | 755302 | B1 | 10/2000 |
| CN | 1675172 | A | 9/2005 | EP | 929513 | B1 | 4/2001 |
| CN | 1222358 | C | 10/2005 | EP | 881924 | B1 | 5/2001 |
| CN | 1732148 | A | 2/2006 | EP | 854858 | B1 | 6/2001 |
| CN | 1735460 | A | 2/2006 | EP | 815073 | B1 | 7/2001 |
| CN | 1245489 | C | 3/2006 | EP | 1144114 | A3 | 9/2001 |
| CN | 1740183 | A | 3/2006 | EP | 1091804 | B1 | 2/2002 |
| CN | 1745062 | A | 3/2006 | EP | 944585 | B1 | 4/2002 |
| CN | 1767895 | A | 5/2006 | EP | 1000019 | B1 | 2/2003 |
| CN | 1260009 | C | 6/2006 | EP | 911339 | B1 | 4/2003 |
| CN | 1266424 | C | 7/2006 | EP | 1344770 | | 9/2003 |
| CN | 1270543 | C | 8/2006 | EP | 1216268 | B1 | 11/2003 |
| CN | 1274671 | C | 9/2006 | EP | 1350788 | A3 | 11/2003 |
| CN | 1274699 | C | 9/2006 | EP | 1003607 | B1 | 12/2003 |
| CN | 1835915 | A | 9/2006 | EP | 1003716 | B1 | 2/2004 |
| CN | 1279088 | C | 10/2006 | EP | 1313743 | B1 | 3/2004 |
| CN | 1847288 | A | 10/2006 | EP | 1414567 | A1 | 5/2004 |
| CN | 1283620 | C | 11/2006 | EP | 1427695 | A1 | 6/2004 |
| CN | 1857775 | A | 11/2006 | EP | 1438133 | A1 | 7/2004 |
| CN | 1289539 | C | 12/2006 | EP | 1019190 | B1 | 12/2004 |
| CN | 1293942 | C | 1/2007 | EP | 1140801 | B1 | 2/2005 |
| CN | 1906150 | A | 1/2007 | EP | 1395547 | B1 | 3/2005 |
| CN | 1914154 | A | 2/2007 | EP | 1001928 | B1 | 4/2005 |
| CN | 1914155 | A | 2/2007 | EP | 1521736 | A1 | 4/2005 |
| CN | 1914156 | A | 2/2007 | EP | 1521737 | A1 | 4/2005 |
| CN | 1914157 | A | 2/2007 | EP | 1521738 | A2 | 4/2005 |
| CN | 1914158 | A | 2/2007 | EP | 1603865 | A1 | 12/2005 |
| CN | 1914159 | A | 2/2007 | EP | 1324976 | B1 | 2/2006 |
| CN | 1914160 | A | 2/2007 | EP | 1214975 | B1 | 3/2006 |
| CN | 1914161 | A | 2/2007 | EP | 1324978 | B1 | 3/2006 |
| CN | 1914162 | A | 2/2007 | EP | 1648860 | A1 | 4/2006 |
| CN | 1914165 | A | 2/2007 | EP | 891323 | B1 | 6/2006 |
| CN | 1914166 | A | 2/2007 | EP | 1226147 | B1 | 6/2006 |
| CN | 1914167 | A | 2/2007 | EP | 1438317 | B1 | 6/2006 |
| CN | 1914216 | A | 2/2007 | EP | 1682561 | A1 | 7/2006 |
| CN | 1307237 | C | 3/2007 | EP | 1448668 | B1 | 8/2006 |
| CN | 1315790 | C | 5/2007 | EP | 1587621 | B1 | 8/2006 |
| CN | 1318432 | C | 5/2007 | EP | 1713759 | A1 | 10/2006 |
| CN | 1997624 | A | 7/2007 | EP | 1713761 | A1 | 10/2006 |
| CN | 1331843 | C | 8/2007 | EP | 1713762 | A1 | 10/2006 |

| | | | | | | |
|---|---|---|---|---|---|---|
| EP | 1713766 | A1 | 10/2006 | JP | 3205587 | A | 9/1991 |
| EP | 1716102 | A2 | 11/2006 | JP | 1627124 | C | 11/1991 |
| EP | 1716103 | A1 | 11/2006 | JP | 1627146 | C | 11/1991 |
| EP | 1716104 | A1 | 11/2006 | JP | 3069915 | B | 11/1991 |
| EP | 1716105 | A1 | 11/2006 | JP | 3285878 | A | 12/1991 |
| EP | 1716106 | A1 | 11/2006 | JP | 1642102 | C | 2/1992 |
| EP | 1716107 | A1 | 11/2006 | JP | 4012248 | Y2 | 3/1992 |
| EP | 1716109 | A2 | 11/2006 | JP | 4057050 | U | 5/1992 |
| EP | 1610893 | B1 | 3/2007 | JP | 4166155 | A | 6/1992 |
| EP | 1621531 | B1 | 3/2007 | JP | 4230254 | A | 8/1992 |
| EP | 1438132 | B1 | 4/2007 | JP | 4057050 | B | 9/1992 |
| EP | 1799697 | A1 | 6/2007 | JP | 4060532 | B | 9/1992 |
| EP | 1713764 | B1 | 8/2007 | JP | 4118676 | U | 10/1992 |
| EP | 1713816 | B1 | 8/2007 | JP | 4128141 | U | 11/1992 |
| EP | 1825914 | A1 | 8/2007 | JP | 1729140 | C | 1/1993 |
| EP | 1448620 | B1 | 6/2008 | JP | 1811422 | C | 12/1993 |
| EP | 1817108 | B1 | 6/2008 | JP | 7025841 | Y2 | 6/1995 |
| EP | 1713760 | B1 | 7/2008 | JP | 7188144 | A | 7/1995 |
| EP | 1571172 | B1 | 10/2008 | JP | 2037346 | C | 3/1996 |
| EP | 1988998 | A1 | 11/2008 | JP | 8504814 | A | 5/1996 |
| EP | 1265832 | B1 | 5/2009 | JP | 8157795 | A | 6/1996 |
| EP | 1592659 | B1 | 7/2009 | JP | 2098106 | C | 10/1996 |
| EP | 1586598 | B1 | 9/2009 | JP | 02521777 | Y2 | 1/1997 |
| EP | 2098106 | A1 | 9/2009 | JP | 02623448 | B2 | 6/1997 |
| EP | 1567478 | B1 | 10/2009 | JP | 9505586 | A | 6/1997 |
| EP | 1682559 | B1 | 12/2009 | JP | 9512013 | A | 12/1997 |
| EP | 1630166 | B1 | 2/2010 | JP | 10505101 | A | 5/1998 |
| FR | 1544656 | A | 11/1968 | JP | 10506911 | A | 7/1998 |
| FR | 2015115 | A5 | 4/1970 | JP | 10509954 | A | 9/1998 |
| FR | 1603513 | A | 5/1971 | JP | 02818503 | B2 | 10/1998 |
| FR | 2069411 | A5 | 9/1971 | JP | 10512879 | A | 12/1998 |
| FR | 2845379 | B1 | 12/2004 | JP | 11501660 | A | 2/1999 |
| FR | 2873696 | A1 | 2/2006 | JP | 11504262 | A | 4/1999 |
| FR | 2873696 | B1 | 10/2006 | JP | 02911608 | B2 | 6/1999 |
| GB | 0219474 | A | 7/1924 | JP | 11507297 | A | 6/1999 |
| GB | 1104140 | A | 2/1968 | JP | 03001298 | B2 | 1/2000 |
| GB | 1203702 | A | 9/1970 | JP | 03069915 | B2 | 7/2000 |
| GB | 1213175 | A | 11/1970 | JP | 2001500135 | A | 1/2001 |
| GB | 1429169 | A | 3/1976 | JP | 2001506250 | A | 5/2001 |
| GB | 1429621 | A | 3/1976 | JP | 2001512097 | A | 8/2001 |
| GB | 1436932 | A | 5/1976 | JP | 03205587 | B2 | 9/2001 |
| GB | 1458322 | A | 12/1976 | JP | 2001516640 | A | 10/2001 |
| GB | 1482909 | A | 8/1977 | JP | 03285878 | B2 | 5/2002 |
| GB | 2007521 | A | 5/1979 | JP | 2002517473 | A | 6/2002 |
| GB | 1565443 | A | 4/1980 | JP | 03320424 | B2 | 9/2002 |
| GB | 1594694 | A | 8/1981 | JP | 2002533321 | A | 10/2002 |
| GB | 2007521 | B | 6/1982 | JP | 03380543 | B2 | 2/2003 |
| HK | 1025950 | A1 | 7/2003 | JP | 2003510385 | A | 3/2003 |
| HK | 1026383 | A1 | 7/2004 | JP | 2003526688 | A | 9/2003 |
| HK | 1052364 | A1 | 5/2007 | JP | 03478399 | B2 | 12/2003 |
| JP | 48028423 | Y1 | 8/1973 | JP | 2004501058 | A | 1/2004 |
| JP | 48028423 | B | 9/1973 | JP | 2004507550 | A | 3/2004 |
| JP | 49043924 | Y1 | 12/1974 | JP | 03519410 | B2 | 4/2004 |
| JP | 50059324 | U | 6/1975 | JP | 03535172 | B2 | 6/2004 |
| JP | 50059326 | U | 6/1975 | JP | 03553952 | B2 | 8/2004 |
| JP | 51007649 | B | 3/1976 | JP | 2004534032 | A | 11/2004 |
| JP | 52012698 | B | 4/1977 | JP | 2004535929 | A | 12/2004 |
| JP | 1013127 | C | 9/1980 | JP | 03621133 | B2 | 2/2005 |
| JP | 55047031 | B | 11/1980 | JP | 2005503410 | A | 2/2005 |
| JP | 57156454 | U | 10/1982 | JP | 2005505610 | A | 2/2005 |
| JP | 57156455 | U | 10/1982 | JP | 2005505611 | A | 2/2005 |
| JP | 57179144 | U | 11/1982 | JP | 2005510588 | A | 4/2005 |
| JP | 1136333 | C | 2/1983 | JP | 2005510605 | A | 4/2005 |
| JP | 58067658 | U | 5/1983 | JP | 2004509942 | | 10/2005 |
| JP | 58126892 | U | 8/1983 | JP | 2005533095 | A | 11/2005 |
| JP | 1170710 | C | 10/1983 | JP | 2005533096 | A | 11/2005 |
| JP | 58159452 | U | 10/1983 | JP | 2005538075 | A | 12/2005 |
| JP | 60044295 | A | 3/1985 | JP | 03739404 | B2 | 1/2006 |
| JP | 60044295 | B | 10/1985 | JP | 2004535929 | | 1/2006 |
| JP | 62294691 | A | 12/1987 | JP | 2006000451 | A | 1/2006 |
| JP | 63135363 | U | 9/1988 | JP | 20045340232 | | 1/2006 |
| JP | 1013127 | Y2 | 4/1989 | JP | 2006511591 | A | 4/2006 |
| JP | 1209830 | A | 8/1989 | JP | 2006519797 | A | 8/2006 |
| JP | 1136333 | U | 9/1989 | JP | 2006528616 | A | 12/2006 |
| JP | 1050220 | B | 10/1989 | JP | 2007083057 | A | 4/2007 |
| JP | 1173751 | U | 12/1989 | JP | 2007509885 | A | 4/2007 |
| JP | 1565159 | C | 6/1990 | JP | 2007509886 | A | 4/2007 |
| JP | 3001298 | B | 1/1991 | JP | 2007509887 | A | 4/2007 |
| JP | 1615749 | C | 8/1991 | JP | 2007519516 | A | 7/2007 |

| | | | | | | |
|---|---|---|---|---|---|---|
| JP | 2007519663 A | 7/2007 | | WO | WO9913983 A1 | 3/1999 |
| JP | 2007519664 A | 7/2007 | | WO | WO99/52632 | 10/1999 |
| JP | 2007519666 A | 7/2007 | | WO | WO9964155 A1 | 12/1999 |
| JP | 2007519667 A | 7/2007 | | WO | WO0001485 A2 | 1/2000 |
| JP | 2007519670 A | 7/2007 | | WO | WO0037431 A1 | 6/2000 |
| JP | 2007519671 A | 7/2007 | | WO | WO01/14392 | 3/2001 |
| JP | 2007519672 A | 7/2007 | | WO | WO0121684 A1 | 3/2001 |
| JP | 2007519673 A | 7/2007 | | WO | WO0136429 A1 | 5/2001 |
| JP | 2007519674 A | 7/2007 | | WO | WO0168247 A2 | 9/2001 |
| JP | 2007519675 A | 7/2007 | | WO | WO02/13964 | 2/2002 |
| JP | 2007519677 A | 7/2007 | | WO | WO0211108 A1 | 2/2002 |
| JP | 2007522122 A | 8/2007 | | WO | WO0213964 A2 | 2/2002 |
| JP | 2007115936 | 10/2007 | | WO | WO0218392 A1 | 3/2002 |
| JP | 04012248 B2 | 11/2007 | | WO | WO0226698 A1 | 4/2002 |
| JP | 2006515323 | 2/2008 | | WO | WO0230854 A2 | 4/2002 |
| JP | 04057050 B2 | 3/2008 | | WO | WO0253527 A1 | 7/2002 |
| JP | 04060532 B2 | 3/2008 | | WO | WO02092551 A2 | 11/2002 |
| JP | 2006512918 | 3/2008 | | WO | WO03011457 A1 | 2/2003 |
| JP | 2008515831 A | 5/2008 | | WO | WO03018540 A1 | 3/2003 |
| JP | 2008516907 A | 5/2008 | | WO | WO03024919 A1 | 3/2003 |
| JP | 04118676 B2 | 7/2008 | | WO | WO03031392 A1 | 4/2003 |
| JP | 04128141 B2 | 7/2008 | | WO | WO03033141 A1 | 4/2003 |
| JP | 04166155 B2 | 10/2008 | | WO | WO03033509 A1 | 4/2003 |
| JP | 04230254 B2 | 2/2009 | | WO | WO03046019 A1 | 6/2003 |
| KR | 198802621 Y1 | 7/1988 | | WO | WO03046049 A1 | 6/2003 |
| KR | 198802296 B | 10/1988 | | WO | WO03068729 A1 | 8/2003 |
| KR | 198802296 B1 | 10/1988 | | WO | WO03076394 A1 | 9/2003 |
| KR | 199003458 B1 | 5/1990 | | WO | WO2004007431 A1 | 1/2004 |
| KR | 199008166 B1 | 11/1990 | | WO | WO2004007432 A1 | 1/2004 |
| KR | 199104132 B1 | 6/1991 | | WO | WO2004007435 A2 | 1/2004 |
| KR | 199205087 Y1 | 7/1992 | | WO | WO2004007508 A2 | 1/2004 |
| KR | 2006132885 A | 12/2006 | | WO | WO0168247 A8 | 6/2004 |
| MX | 2004PA002764 A | 6/2004 | | WO | WO2004060855 A1 | 7/2004 |
| NL | 197700262 A | 7/1977 | | WO | WO2004064994 A2 | 8/2004 |
| NL | 188158 C | 4/1992 | | WO | WO2004065352 A2 | 8/2004 |
| SU | 677650 A | 7/1979 | | WO | WO2004080924 A2 | 9/2004 |
| TW | 387874 B | 4/2000 | | WO | WO2004080948 A1 | 9/2004 |
| TW | 400249 B | 8/2000 | | WO | WO2004087314 A1 | 10/2004 |
| TW | 453983 B | 9/2001 | | WO | WO2005019160 A1 | 3/2005 |
| TW | 453985 B | 9/2001 | | WO | WO2005/042547 | 5/2005 |
| TW | 455576 B | 9/2001 | | WO | WO2005042156 A1 | 5/2005 |
| TW | 457244 B | 10/2001 | | WO | WO2005042157 A2 | 5/2005 |
| TW | 458959 B | 10/2001 | | WO | WO2005042547 A1 | 5/2005 |
| TW | 519496 B | 2/2003 | | WO | WO2005042549 A1 | 5/2005 |
| TW | 527340 B | 4/2003 | | WO | WO2005073167 A1 | 8/2005 |
| TW | 576837 B | 2/2004 | | WO | WO2005073168 A1 | 8/2005 |
| TW | 580489 B | 3/2004 | | WO | WO2005073169 A1 | 8/2005 |
| TW | 580490 B | 3/2004 | | WO | WO2005073170 A1 | 8/2005 |
| TW | 584623 B | 4/2004 | | WO | WO2005073171 A1 | 8/2005 |
| TW | 592821 B | 6/2004 | | WO | WO2005073172 A1 | 8/2005 |
| TW | 226345 B | 1/2005 | | WO | WO2005073173 A1 | 8/2005 |
| TW | 233438 B | 6/2005 | | WO | WO2005073174 A1 | 8/2005 |
| TW | 245780 B | 12/2005 | | WO | WO2005073175 A1 | 8/2005 |
| TW | 266650 B | 11/2006 | | WO | WO2005073176 A1 | 8/2005 |
| WO | WO7900193 A1 | 4/1979 | | WO | WO2005073178 A2 | 8/2005 |
| WO | WO9414752 A1 | 7/1994 | | WO | WO2005073179 A1 | 8/2005 |
| WO | WO9514659 A1 | 6/1995 | | WO | WO2005073241 A1 | 8/2005 |
| WO | WO9528228 A1 | 10/1995 | | WO | WO2006040023 A1 | 4/2006 |
| WO | WO9529153 A1 | 11/1995 | | WO | WO2006042675 A2 | 4/2006 |
| WO | WO9611182 A1 | 4/1996 | | WO | WO2005073166 A3 | 3/2007 |
| WO | WO9616022 A1 | 5/1996 | | WO | WO2007051374 A1 | 5/2007 |
| WO | WO9622968 A1 | 8/1996 | | WO | WO2007096274 A1 | 8/2007 |
| WO | WO9629303 A1 | 9/1996 | | WO | WO2007115936 A2 | 10/2007 |
| WO | WO9703040 A1 | 1/1997 | | WO | WO2008008926 A2 | 1/2008 |
| WO | WO9712857 A1 | 4/1997 | | WO | WO2008008928 A2 | 1/2008 |
| WO | WO9724183 A1 | 7/1997 | | WO | WO2008008929 A2 | 1/2008 |
| WO | WO9736855 A2 | 10/1997 | | WO | WO2008008930 A2 | 1/2008 |
| WO | WO9811051 A1 | 3/1998 | | WO | WO2008028843 A1 | 3/2008 |
| WO | WO9827054 A1 | 6/1998 | | WO | WO2008062058 A1 | 5/2008 |
| WO | WO9906146 A2 | 2/1999 | | | | |
| WO | WO9906356 | 2/1999 | | | | |
| WO | WO9906359 A1 | 2/1999 | | | | |

OTHER PUBLICATIONS

U.S. Appl. No. 09/121,105.

PROCESS FOR MAKING AND REFINING 3-PENTENENITRILE, AND FOR REFINING 2-METHYL-3-BUTENENITRILE

CROSS-REFERENCE TO RELATED APPLICATION

This application claims the benefit of the filing date of U.S. Provisional Application No. 61/021,217, filed on Jan. 15, 2008, the entire contents of which are incorporated herein by reference.

FIELD OF THE INVENTION

The invention relates to an integrated process for the hydrocyanation of 1,3-butadiene to produce 3-pentenenitriles and other unsaturated nitriles and for refining of the pentenenitriles. More particularly, this invention relates to a continuous process for the hydrocyanation of 1,3-butadiene using a catalyst composition comprising a zero-valent nickel and at least one bidentate phosphorus-containing ligand, and subsequent refining of the reaction mixture produced to obtain separate streams of 3-pentenenitrile and 2-methyl-3-butenenitrile.

BACKGROUND OF THE INVENTION

3-Pentenenitrile (3PN) is an important intermediate in the production of adiponitrile (ADN). ADN is of particular interest because it is a commercially versatile and important intermediate in the industrial production of nylon polyamides useful in forming films, fibers, and molded articles.

It is well known in the art that 3PN may be formed through a series of reactions as illustrated in Equations 1 and 2 below,

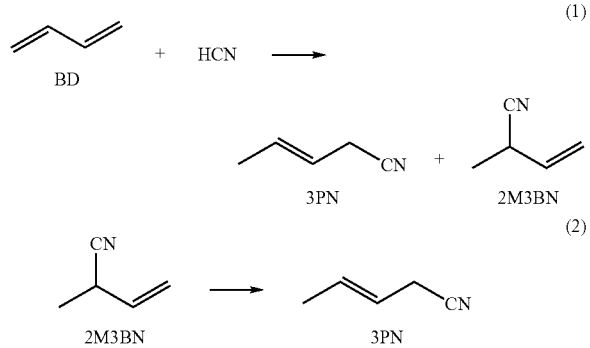

wherein BD is 1,3-butadiene, HCN is hydrogen cyanide, and 2M3BN is the BD hydrocyanation co-product 2-methyl-3-butenenitrile. U.S. Pat. No. 3,496,215 describes the catalytic hydrocyanation of BD (equation 1) in the presence of $NiL_4$ complexes wherein L is a monodentate phosphorus-containing ligand. The relative amounts of 3PN and 2M3BN can be dependent upon the catalyst utilized in this chemical reaction. U.S. Pat. No. 3,536,748 describes the catalytic isomerization of 2M3BN to 3PN (equation 2) in the presence of $NiL_4$ complexes.

U.S. Pat. No. 3,536,748 discloses that in the presence of HCN, the nickel complex preferentially catalyzes formation of undesired, six-carbon, saturated dinitrile (2-methylglutaronitrile, MGN) from 2M3BN (see Equation 3 below). This patent notes that, because of the overriding competitive hydrocyanation reaction, for the isomerization of 2M3BN to 3PN it is necessary to avoid the presence of large amounts of HCN, for example any amount of the order of or in excess of 1:1 mole ratio with the 2M3BN starting material. The reference further discloses that HCN has no significant effect per se on the isomerization reaction, its presence in minor amounts in the starting material can be tolerated if necessary, and the isomerization process is preferably conducted in the absence of HCN.

U.S. Pat. No. 6,169,198 discloses that hydrocyanation of BD to prepare ADN can generally be divided into three steps. The first is synthesis of mononitriles by hydrocyanation of BD (as in Equation 1 above), for which the selectivity for the linear 3PN is about 70% or less, depending on the catalyst used. The second is isomerization of the 2M3BN present in the mixtures to 3PN (as in Equation 2 above) and isomerization of 3PN to various linear pentenenitriles; the third is synthesis of dinitriles. Also disclosed is a preferred embodiment in which the ratio of the amounts of 3PN to 2M3BN obtained in the monoaddition of HCN onto the BD-containing hydrocarbon mixture is at least 5:1, preferably at least 10:1, in particular at least 20:1, with a catalyst comprising at least one metallocene-phosphorus(III)-nickel(0) complex. The reference further discloses that it is generally possible to dispense with division of the process for preparing ADN into the three steps of monoaddition of HCN onto a BD-containing hydrocarbon mixture; isomerization; addition of HCN onto 4-pentenenitrile (4PN) formed in situ; and the addition of 2 mole equivalents of HCN onto a BD-containing hydrocarbon mixture can be designed as a one-stage process.

In recent years, a new class of catalysts has been described for the transformations of Equations 1 and 2. U.S. Pat. Nos. 5,512,695; 5,512,696; 5,523,453; 5,663,369; 5,688,986; 5,693,843; 5,723,641; 5,821,378; 5,959,135; 5,981,772; 6,020,516; 6,127,567; 6,171,996; 6,171,997; and WO99/52632 describe the use of diphosphite and diphosphinite nickel complexes as catalysts for the hydrocyanation of BD or 3PN and the isomerization of 2M3BN to 3PN. In general, this class of catalysts is characterized by greater catalytic activity and resistance to HCN-derived degradation reactions compared to the catalysts comprising nickel complexes of monodentate phosphites and phosphinites. As a result, this new class of catalysts may generally be used effectively at much lower concentrations and over a broader range of reaction conditions. U.S. Pat. Nos. 5,821,378; 5,981,772 and 6,020,516 describe the capability of a limited number of these catalyst systems to isomerize 2M3BN at the same temperature at which BD is hydrocyanated and disclose improved processes for liquid phase hydrocyanation of diolefinic compounds and subsequent isomerization of the resulting nonconjugated 2-alkyl-3-monoalkenenitriles.

A high yield process for the production of 3PN in which BD hydrocyanation and 2M3BN isomerization occur concurrently in the same reaction zone would be desirable because such a process would require fewer reaction and process separation steps (and the associated equipment and operating costs) than a 3PN production process in which the hydrocyanation and isomerization reactions were performed, for example, in separate reaction zones under reaction conditions optimized independently for BD hydrocyanation to 3PN or for 2M3BN isomerization to 3PN. A 3PN process integrated with a pentenenitrile refining process would be advantageous in that the integration of the refining steps with the concurrent BD hydrocyanation/2M3BN isomerization, and a reaction mixture wherein the 2M3BN concentration is maintained below about 15 weight percent of the total mass of the reaction mixture, would facilitate overall process simplification and could provide reduced capital investment and reduced cost of manufacture, as compared to a 3PN production process in which BD hydrocyanation and 2M3BN isomerization were not performed concurrently in the same reaction zone. Process simplification could be achieved, for example, through elimination of a dedicated 2M3BN isomerization reactor (in which no concurrent BD hydrocyanation was performed) or elimination of at least one distillation column, or both. Recycle of at least a portion of any unreacted BD to the BD hydrocyanation/2M3BN isomerization reaction zone could improve 3PN yield based on BD. Reduced yield loss to undesired by-products, such as MGN and compounds derived from BD dimerization and/or oligomerization, might also be realized with a combined BD hydrocyanation/2M3BN isomerization process integrated with a pentenenitrile refining process.

SUMMARY OF THE INVENTION

In a first aspect, the present invention provides an integrated, continuous process for the production of 3-pentenenitrile, the refining of 3-pentenenitrile, and the refining of 2-methyl-3-butenenitrile, the process comprising:

(a) contacting, in a reaction zone, a hydrogen cyanide (HCN)-containing feed, a 1,3-butadiene (BD)-containing feed, and a catalyst composition, wherein the catalyst composition comprises a zero-valent nickel and at least one bidentate phosphorus-containing ligand selected from the group consisting of a phosphite, a phosphonite, a phosphinite, a phosphine, a mixed phosphorus-containing ligand, and combinations thereof;

(b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture;

(c) distilling the reaction mixture to obtain a first stream comprising 1,3-butadiene, a second stream comprising 3-pentenenitrile, 2-methyl-3-butenenitrile, (Z)-2-methyl-2-butenenitrile, and optionally 1,3-butadiene, and a third stream comprising the catalyst composition;

(d) distilling the second stream to obtain a fourth stream comprising 1,3-butadiene, a fifth stream comprising 2-methyl-3-butenenitrile, (Z)-2-methyl-2-butenenitrile, and optionally 1,3-butadiene, and a sixth stream comprising 3-pentenenitrile; and (e) distilling the fifth stream to obtain a seventh stream comprising 1,3-butadiene, an eighth stream comprising (Z)-2-methyl-2-butenenitrile, and a ninth stream comprising 2-methyl-3-butenenitrile.

Another aspect of the present invention is the process wherein at least one distilling process separately obtains a combination stream and an additional stream; wherein the distilling process is selected from the group consisting of (c) distilling the reaction mixture, (d) distilling the second stream, (e) distilling the fifth stream, and combinations thereof;

the combination stream is introduced into at least one partial condenser to obtain a vapor stream and a liquid stream;

when the distilling process is (c) distilling the reaction mixture, the combination stream is stream A, the vapor stream obtained from stream A is the first stream comprising 1,3-butadiene, the liquid stream obtained from stream A is the second stream comprising 3-pentenenitrile, 2-methyl-3-butenenitrile, (Z)-2-methyl-2-butenenitrile, and optionally 1,3-butadiene, and the additional stream is the third stream;

when the distilling process is (d) distilling the second stream, the combination stream is stream B, the vapor stream obtained from stream B is the fourth stream comprising 1,3-butadiene, the liquid stream obtained from stream B is the fifth stream comprising 2-methyl-3-butenenitrile, (Z)-2-methyl-2-butenenitrile, and optionally 1,3-butadiene, and the additional stream is the sixth stream; and when the distilling process is (e) distilling the fifth stream, the combination stream is stream C, the vapor stream obtained from stream C is the seventh stream comprising 1,3-butadiene, the liquid stream obtained from stream C is the eighth stream comprising (Z)-2-methyl-2-butenenitrile, and the additional stream is the ninth stream.

Another aspect of the present invention is the process wherein (c) distilling the reaction mixture obtains a stream A and the third stream; and stream A is introduced into at least one partial condenser to obtain the first stream as a vapor stream comprising 1,3-butadiene and the second stream as a liquid stream comprising 3-pentenenitrile, 2-methyl-3-butenenitrile, (Z)-2-methyl-2-butenenitrile, and optionally 1,3-butadiene.

Another aspect of the present invention is the process wherein (d) distilling the second stream obtains a stream B and the sixth stream; and stream B is introduced into at least one partial condenser to obtain the fourth stream as a vapor stream comprising 1,3-butadiene and the fifth stream as a liquid stream comprising 2-methyl-3-butenenitrile, (Z)-2-methyl-2-butenenitrile, and optionally 1,3-butadiene.

Another aspect of the present invention is the process wherein (e) distilling the fifth stream obtains a stream C and the ninth stream; and stream C is introduced into at least one partial condenser to obtain the seventh stream as a vapor stream comprising 1,3-butadiene and the eighth stream as a liquid stream comprising (Z)-2-methyl-2-butenenitrile.

Another aspect of the present invention is the process wherein distilling the reaction mixture obtains a stream A and the third stream;

stream A is introduced into at least one partial condenser to obtain the first stream as a vapor stream comprising 1,3-butadiene and the second stream as a liquid stream comprising 3-pentenenitrile, 2-methyl-3-butenenitrile, (Z)-2-methyl-2-butenenitrile, and optionally 1,3-butadiene;

distilling the second stream obtains a stream B and the sixth stream;

stream B is introduced into at least one partial condenser to obtain the fourth stream as a vapor stream comprising 1,3-butadiene and the fifth stream as a liquid stream comprising 2-methyl-3-butenenitrile, (Z)-2-methyl-2-butenenitrile, and optionally 1,3-butadiene;

distilling the fifth stream obtains a stream C and the ninth stream; and stream C is introduced into at least one partial condenser to obtain the seventh stream as a vapor stream comprising 1,3-butadiene and the eighth stream as a liquid stream comprising (Z)-2-methyl-2-butenenitrile.

Another aspect of the present invention is the process wherein at least a portion of the ninth stream comprising 2-methyl-3-butenenitrile is returned to the reaction zone.

Another aspect of the present invention is the process wherein at least a portion of the first stream, the fourth stream, the seventh stream, or combinations thereof is returned to the reaction zone.

Another aspect of the present invention is the process wherein at least one of the first stream, the fourth stream, or the seventh stream further comprises butene, and at least a portion of the first stream, the fourth stream, the seventh stream, or combinations thereof is withdrawn to purge at least a portion of the butene prior to returning the stream to the reaction zone.

Another aspect of the invention is the process wherein the total butene content of at least one of the first stream, the fourth stream, or the seventh stream is greater than about 20 percent by weight.

Another aspect of the invention is the process wherein at least a portion of the ninth stream comprising 2-methyl-3-butenenitrile is contacted with at least a portion of the first stream comprising 1,3-butadiene to produce a recycle stream comprising 2-methyl-3-butenenitrile and 1,3-butadiene, and the recycle stream is returned to the reaction zone.

Another aspect of the invention is the process wherein at least a portion of the third stream comprising the catalyst composition is returned to the reaction zone.

Another aspect of the invention is the process wherein at least a portion of the sixth stream comprising 3-pentenenitrile is hydrocyanated to produce a dinitrile product comprising adiponitrile.

Another aspect of the invention is the process wherein the 1,3-butadiene-containing feed comprises 1,3-butadiene which has been distilled to remove an impurity selected from the group consisting of 4-tert-butylcatechol, 4-vinyl-1-cyclohexene, and combinations thereof.

Another aspect of the invention is the process wherein the reaction mixture is distilled in at least one distillation column at less than one atmosphere pressure and with a base temperature of about 120° C. or less.

Another aspect of the invention is the process wherein the second stream is distilled in at least one distillation column at or above one atmosphere pressure and wherein the sixth stream contains less than about 1.0 percent by weight 2-methyl-3-butenenitrile.

Another aspect of the invention is the process wherein the fifth stream is distilled in at least one distillation column and wherein the fifth stream is introduced to the rectifying section of the column.

Another aspect of the present invention is the process wherein the temperature is maintained within a range of about 80° C. to about 140° C.

Another aspect of the present invention is the process wherein the molar ratio of the hydrogen cyanide in the feed to the 1,3-butadiene in the feed is in the range of about 0.90:1.00 to about 1.04:1.00, and the molar ratio of the zero-valent nickel in the feed to the 1,3-butadiene in the feed is in the range of about 0.00005:1.00 to about 0.0050:1.00.

Another aspect of the present invention is the process wherein the bidentate phosphorus-containing ligand is a phosphite ligand selected from a member of the group represented by Formula XXXIII and Formula XXXIV:

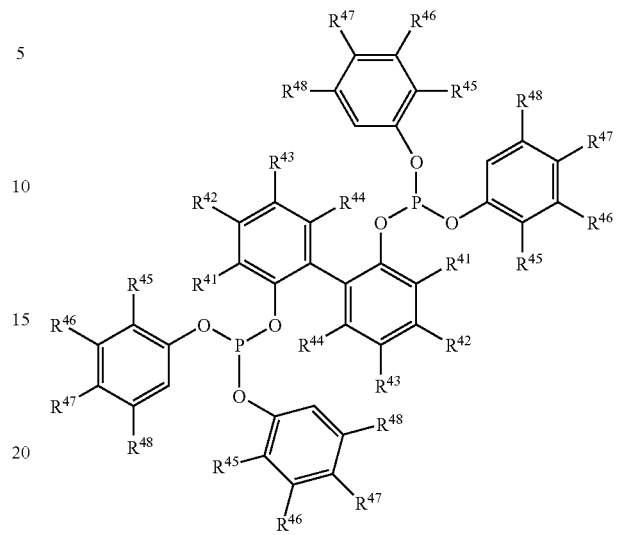

Formula XXXIII

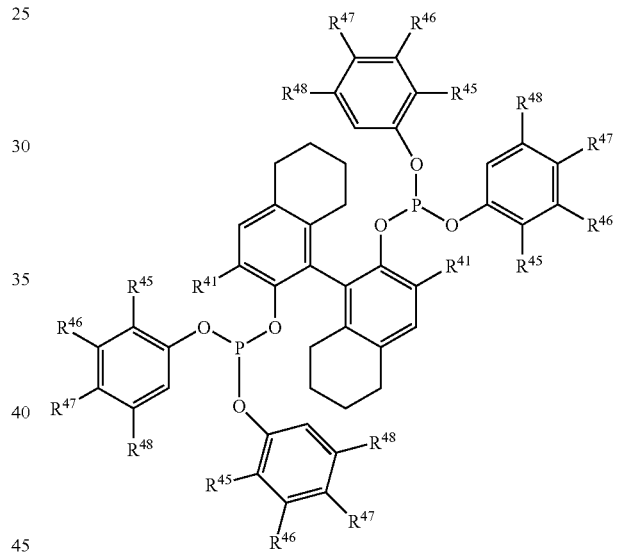

Formula XXXIV wherein $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl.

Another aspect of the present invention is the process wherein the catalyst composition further comprises at least one monodentate phosphite ligand.

In another aspect, the present invention provides an integrated, continuous process for the production of 3-pentenenitrile, the refining of 3-pentenenitrile, and the refining of 2-methyl-3-butenenitrile, the process comprising:

(a) contacting, in a reaction zone, a hydrogen cyanide-containing feed, a butadiene-containing feed, and a catalyst composition, wherein the catalyst composition comprises a zero-valent nickel and at least one bidentate phosphite ligand selected from a member of the group represented by Formulas XXXIII and XXXIV,

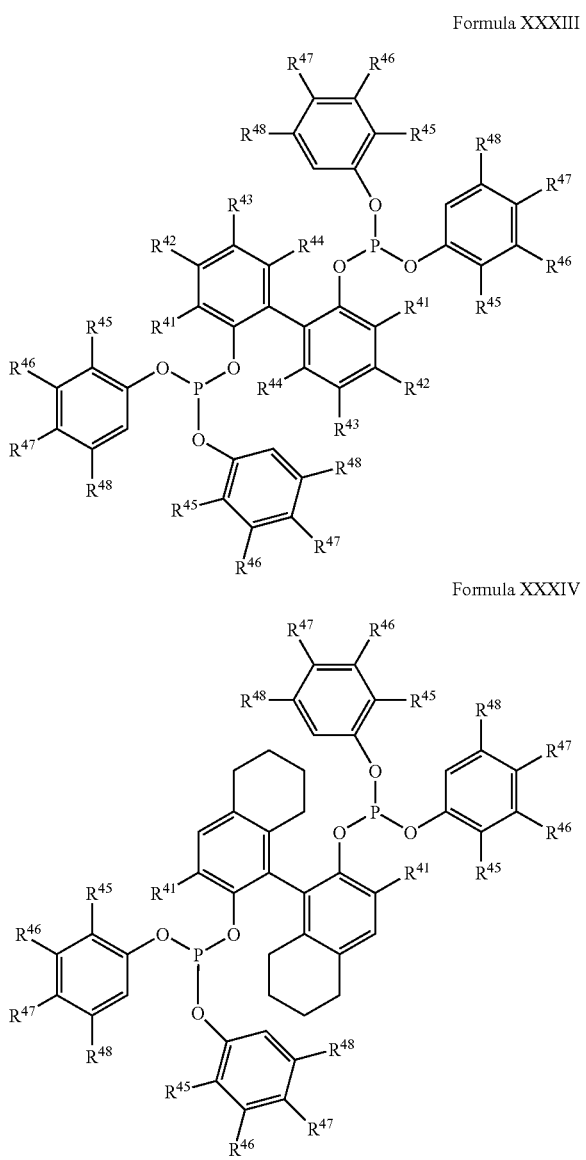

Formula XXXIII

Formula XXXIV wherein $R_1$ and $R_5$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl;

(b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture;

(c) distilling the reaction mixture to obtain a first overhead stream comprising 1,3-butadiene, a first side-draw stream comprising 3-pentenenitrile, 2-methyl-3-butenenitrile, (Z)-2-methyl-2-butenenitrile, and optionally 1,3-butadiene, and a first bottom stream comprising the catalyst composition;

(d) distilling the first side-draw stream to obtain a second overhead stream comprising 1,3-butadiene, a second side-draw stream comprising 2-methyl-3-butenenitrile, (Z)-2-methyl-2-butenenitrile, and optionally 1,3-butadiene, and a second bottom stream comprising 3-pentenenitrile; and (e) distilling the second side-draw stream to obtain a third overhead stream comprising 1,3-butadiene, a third side-draw stream comprising (Z)-2-methyl-2-butenenitrile, and a third bottom stream comprising 2-methyl-3-butenenitrile;

(f) returning at least a portion of the first overhead stream, the second overhead stream, the third overhead stream, or combinations thereof to the reaction zone; and (g) returning at least a portion of the third bottom stream to the reaction zone.

Another aspect of the present invention is the process wherein the catalyst composition further comprises at least one monodentate phosphite ligand.

DETAILED DESCRIPTION OF THE DRAWINGS

FIG. 1 schematically illustrates one embodiment of the processes of the invention.

Figure 2:
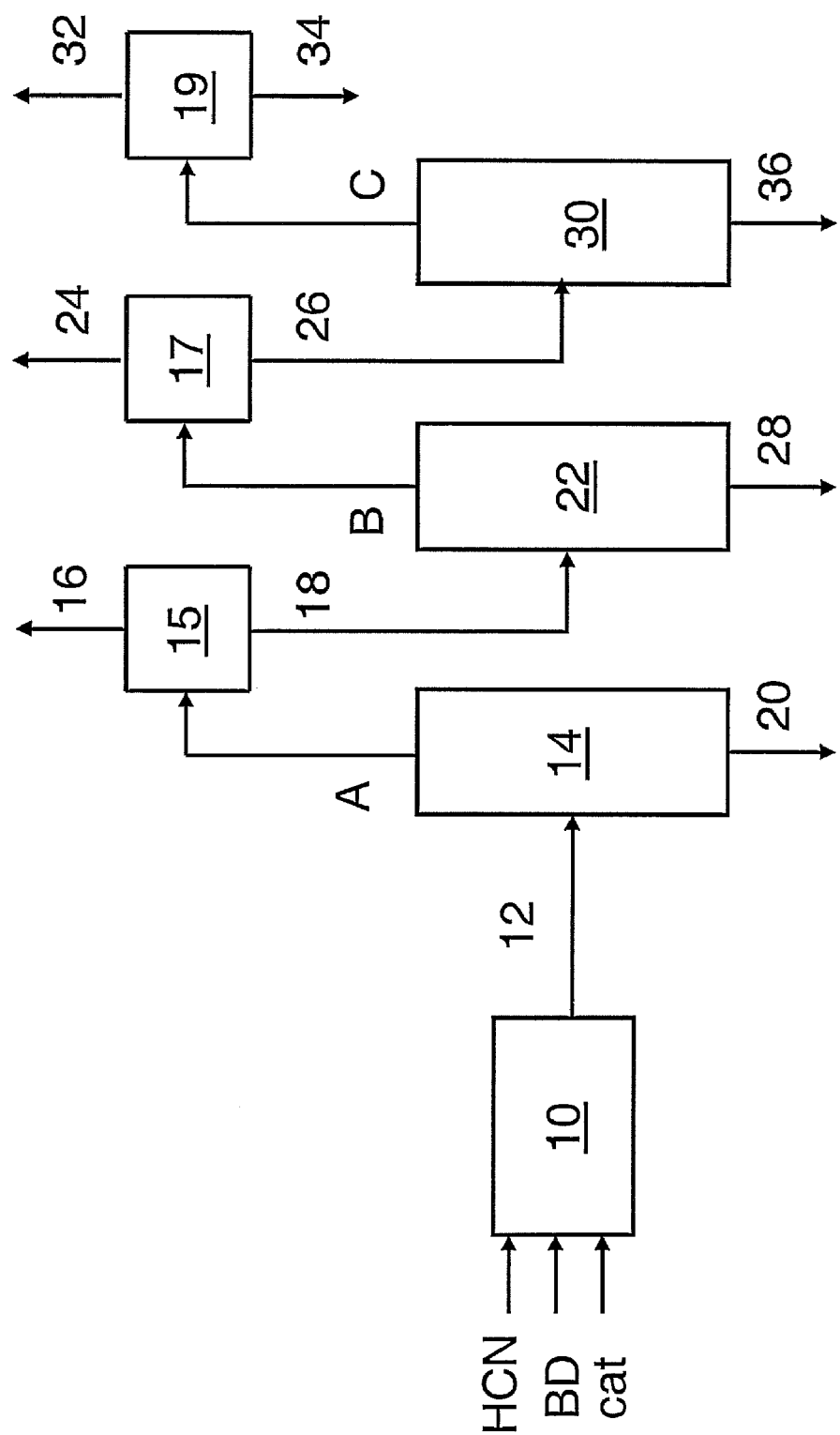

FIG. 2 schematically illustrates another embodiment of the processes of the invention.

Figure 3:
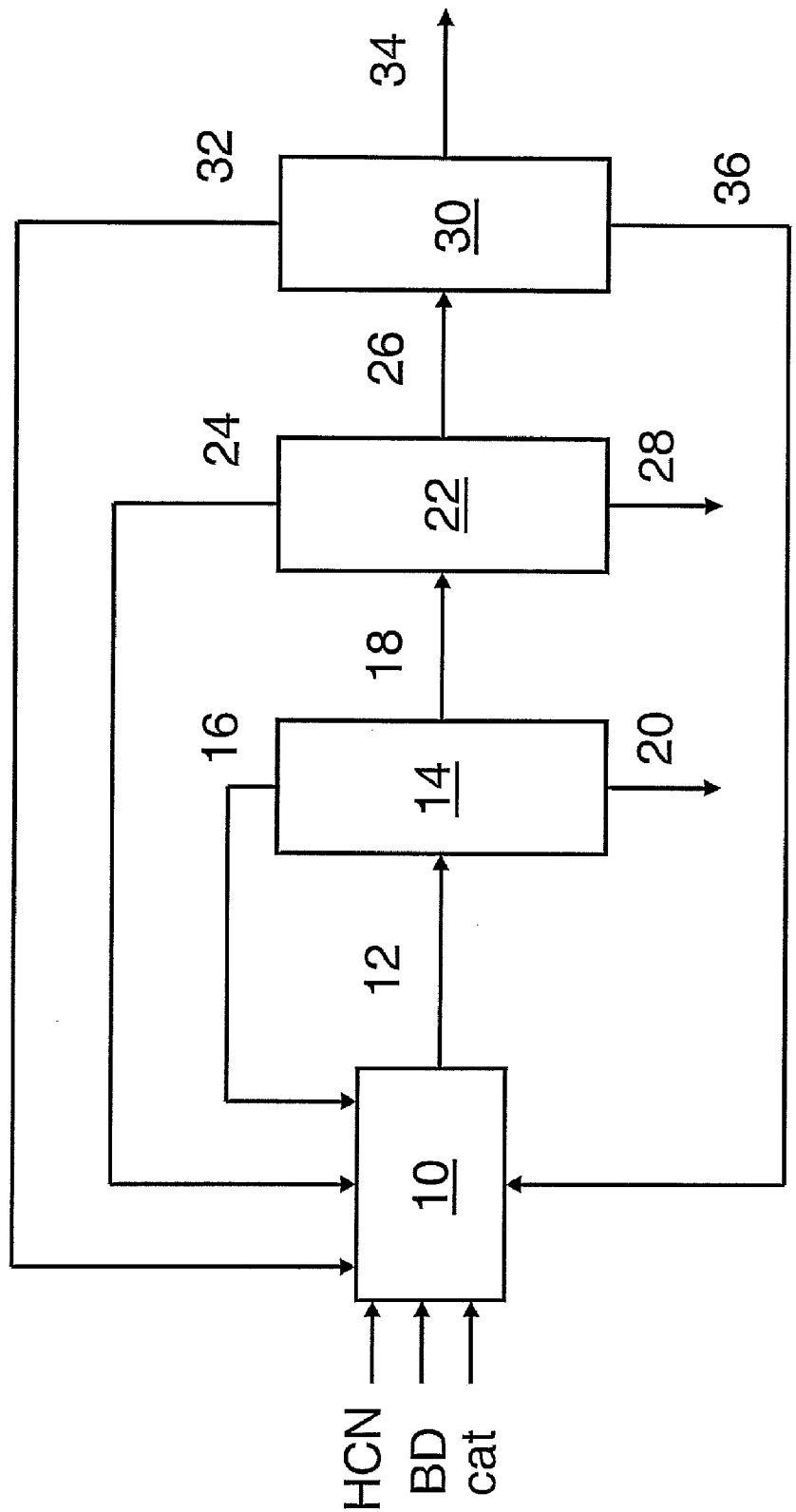

FIG. 3 schematically illustrates one embodiment of the processes of the invention, in which unreacted BD is returned to the reaction zone and 2M3BN is also returned to the reaction zone.

Figure 4:
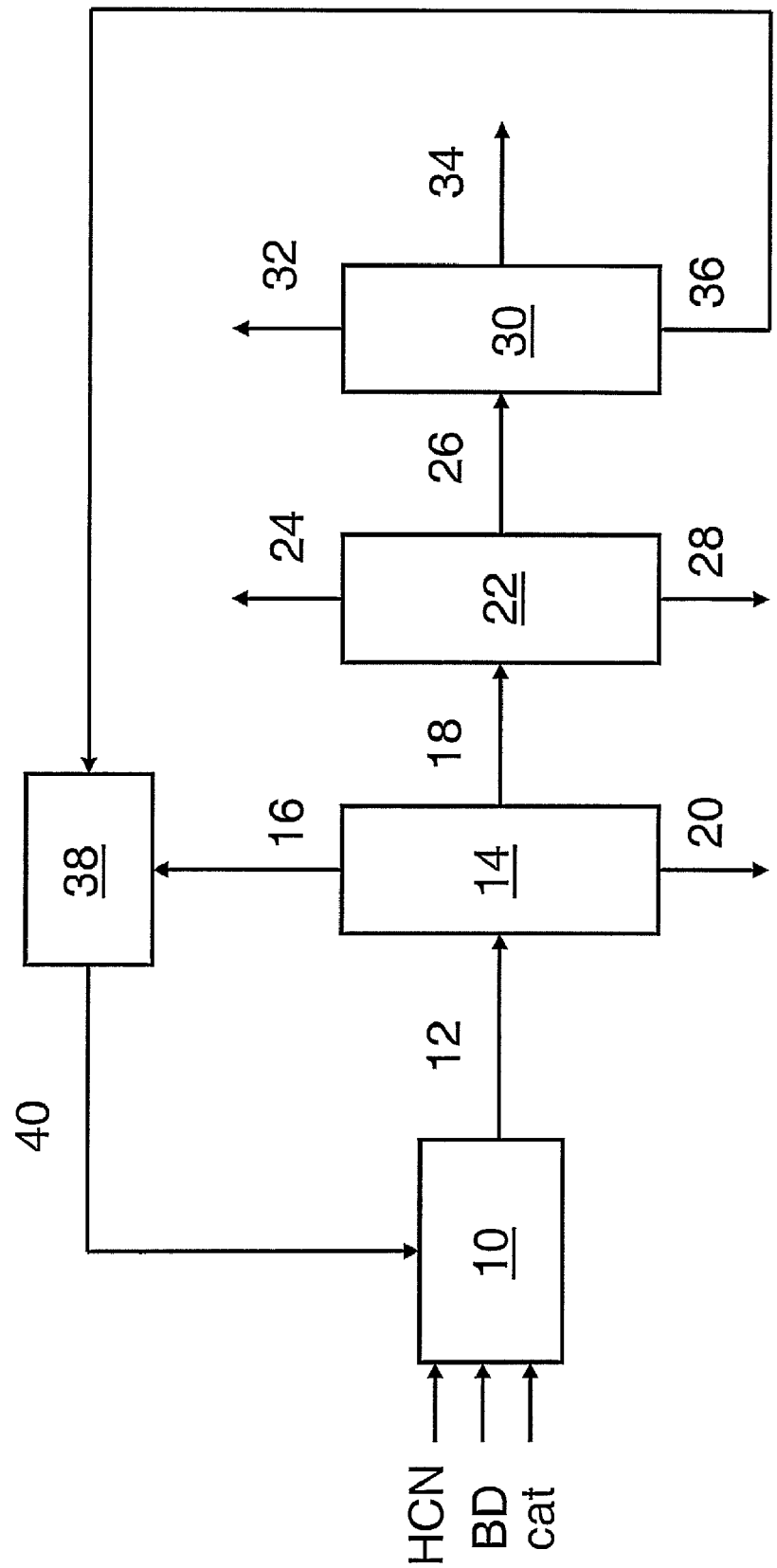

FIG. 4 schematically illustrates one embodiment of the processes of the invention, in which 2M3BN is contacted with unreacted BD to produce a recycle stream which is returned to the reaction zone.

Figure 5:
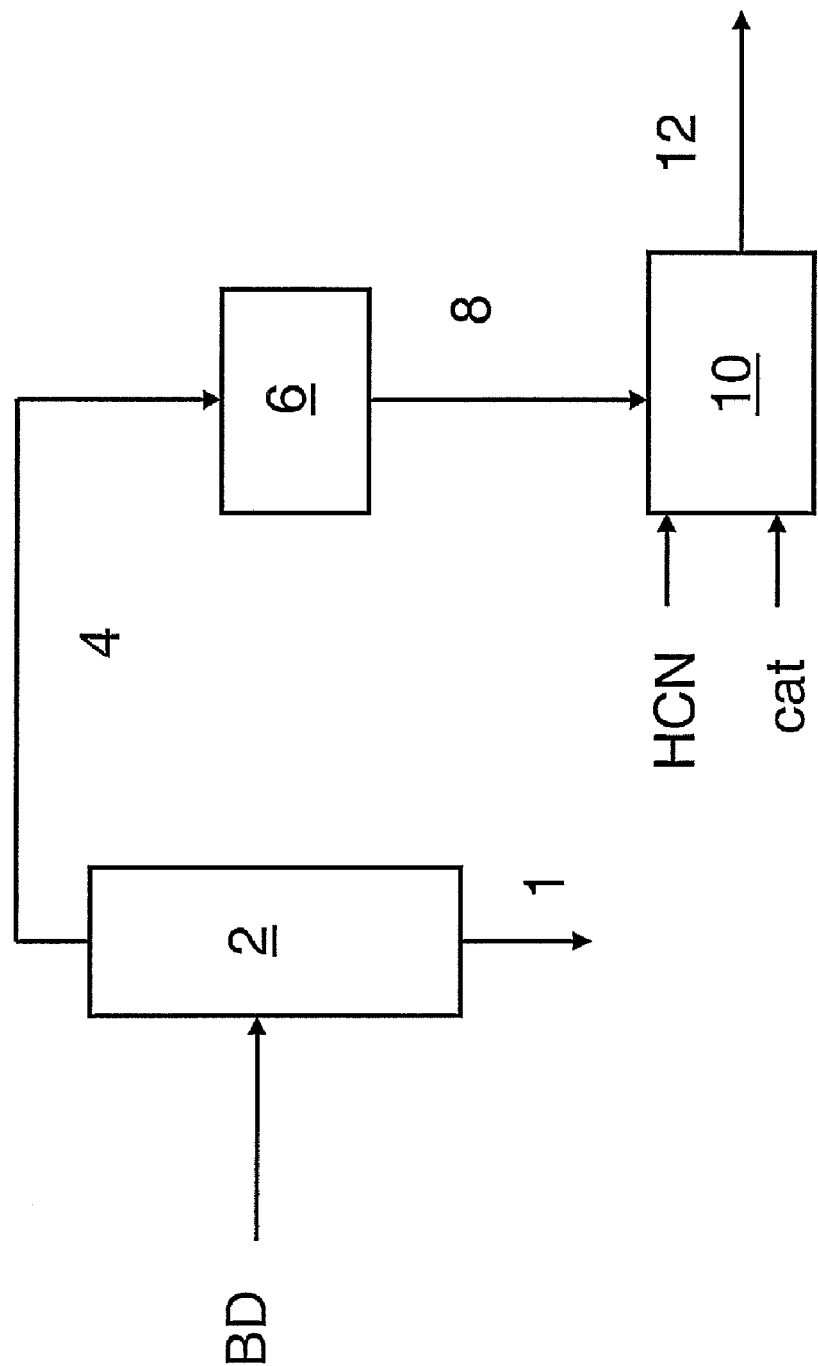

FIG. 5 schematically illustrates one embodiment of the processes of the invention, in which BD is purified prior to being fed to the reaction zone.

DETAILED DESCRIPTION OF THE INVENTION

As used herein, the term "3PN" refers to 3-pentenenitrile and 3-pentenenitriles and includes both cis-3-pentenenitrile (cis-3PN) and trans-3-pentenenitrile (trans-3PN), unless otherwise specified. Similarly, the term "2PN" refers to 2-pentenenitrile and 2-pentenenitriles and includes both cis-2-pentenenitrile (cis-2PN) and trans-2-pentenenitrile (trans-2PN), unless otherwise specified. The term "4PN" refers to 4-pentenenitrile. The term "2M3BN" refers to 2-methyl-3-butenenitrile. The term "2M2BN" refers to 2-methyl-2-butenenitrile and includes both (Z)-2-methyl-2-butenenitrile [(Z)-2M2BN] and (E)-2-methyl-2-butenenitrile [(E)-2M2BN], unless otherwise specified. The term "unsaturated nitriles" includes 2PN, 3PN, 4PN, and methylbutenenitriles 2M3BN and 2M2BN. As used herein, the term "unsaturated nitriles" is synonymous with the term "pentenenitriles" which includes methylbutenenitriles. As used herein, the term "butene" refers to 1-butene, 2-butene, and 2-butenes and includes both cis-2-butene and trans-2-butene, unless otherwise specified.

The invention provides an integrated, continuous process for the production of 3PN, the refining of 3PN, and the refining of 2M3BN. An HCN-containing feed, a BD-containing feed, and a catalyst composition solution are contacted, for example concurrently, in a reaction zone, for example a continuous-stirred-tank-reactor (CSTR), and a residence time in the reaction zone is maintained sufficient to convert about 95% or more of the HCN and to produce a reaction mixture comprising 3PN and 2M3BN, wherein the 2M3BN concentration is maintained below about 15 weight percent of the total mass of the reaction mixture. The reaction mixture is then refined, for example in a series of distillations, to provide refined 3PN and 2M3BN streams. In the first distillation, the reaction mixture from the reaction zone is distilled to obtain a first stream comprising BD, a second stream comprising 3PN, 2M3BN, (Z)-2M2BN and optionally BD, and a third stream comprising the catalyst composition. In the second distillation, the second stream from the first distillation is distilled to obtain a fourth stream comprising BD, a fifth stream comprising 2M3BN, (Z)-2M2BN, and optionally BD, and a sixth stream comprising 3PN. In the third distillation, the fifth stream from the second distillation is distilled to obtain a seventh stream comprising BD, an eighth stream comprising (Z)-2M2BN, and a ninth stream comprising 2M3BN.

Alternatively, the reaction mixture is refined to provide refined 3PN and 2M3BN streams in a series of distillations wherein at least one distilling process separately obtains a combination stream and an additional stream, and the combination stream is introduced into at least one partial condenser to obtain a vapor stream and a liquid stream. For example, the reaction mixture can be distilled in at least one distillation column to obtain a stream A and the third stream, and stream A is introduced into at least one partial condenser to obtain the first stream as a vapor stream comprising BD and the second stream as a liquid stream comprising 3PN, 2M3BN, (Z)-2M2BN, and optionally BD. Similarly, the second stream can be distilled in at least one distillation column to obtain a stream B and the sixth stream, and stream B is introduced into at least one partial condenser to obtain the fourth stream as a vapor stream comprising BD and the fifth stream as a liquid stream comprising 2M3BN, (Z)-2M2BN, and optionally BD. Similarly, the fifth stream can be distilled in at least one distillation column to obtain a stream C and the ninth stream; and stream C is introduced into at least one partial condenser to obtain the seventh stream as a vapor stream comprising BD and the eighth stream as a liquid stream comprising (Z)-2M2BN.

Combinations thereof are also possible, as in, for example, a process wherein distilling the reaction mixture obtains a stream A and the third stream; stream A is introduced into at least one partial condenser to obtain the first stream as a vapor stream comprising BD and the second stream as a liquid stream comprising 3PN, 2M3BN, (Z)-2M2BN, and optionally BD; distilling the second stream obtains a stream B and the sixth stream; stream B is introduced into at least one partial condenser to obtain the fourth stream as a vapor stream comprising BD and the fifth stream as a liquid stream comprising 2M3BN, (Z)-2M2BN, and optionally BD; distilling the fifth stream obtains a stream C and the ninth stream; and stream C is introduced into at least one partial condenser to obtain the seventh stream as a vapor stream comprising BD and the eighth stream as a liquid stream comprising (Z)-2M2BN.

In processes falling within the scope of the present invention, the hydrocyanation and isomerization reactions of Equations 1 and 2 (above) can be carried out concurrently and continuously in the same reaction zone, for example under high BD and HCN conversion conditions.

The hydrocyanation and isomerization processes may be performed using a catalyst composition comprising a zero-valent nickel and at least one multidentate phosphorus-containing (P-containing) ligand, wherein the P-containing ligand is selected from the group consisting of a phosphite, a phosphonite, a phosphinite, a phosphine, and a mixed P-containing ligand or a combination of such members. As used herein, the term "mixed P-containing ligand" means a multidentate phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

The catalyst may comprise at least one monodentate P-containing ligand selected from the group consisting of a phosphite, a phosphonite, a phosphinite, and a phosphine or a combination of such members, provided that the monodentate P-containing ligand does not detract from the beneficial aspects of the invention. The monodentate P-containing ligand may be present as an impurity from the synthesis of the P-containing ligand, or the monodentate P-containing ligand may be added as a single or additional component of the catalyst. The monodentate P-containing ligand may be a mixture of P-containing ligands.

As used herein, the term "catalyst" includes within its meaning a catalyst precursor composition, indicating that that the zero-valent nickel at some point becomes bound to at least one P-containing ligand, and further in all likelihood, additional reactions occur during hydrocyanation and isomerization, such as, for example, complexing of the initial catalyst composition to an ethylenically unsaturated compound. As used herein, the term "catalyst" also includes within its meaning recycled catalyst, that is, a catalyst comprising a zero-valent nickel and at least one P-containing ligand which, having been used in the process of the invention, is returned or may be returned to the process and used again.

The term "hydrocarbyl" is well known in the art and designates a hydrocarbon molecule from which at least one hydrogen atom has been removed. Such molecules can contain single, double, or triple bonds.

The term "aryl" is well-known in the art and designates an aromatic hydrocarbon molecule from which at least one hydrogen atom has been removed. Examples of suitable aryl groups include, for example, those containing 6 to 10 carbon atoms, which can be unsubstituted or singly or multiply substituted. Suitable substituents include, for example, $C_1$ to $C_4$ hydrocarbyl, or halogen such as fluorine, chlorine, or bromine, or halogenated hydrocarbyl such as trifluoromethyl, or aryl such as phenyl.

The P-containing ligands of the Ni(0) complexes and the free P-containing ligands may be monodentate or multidentate, for example bidentate or tridentate. The term "bidentate" is well known in the art and means both phosphorus atoms of the ligand are bonded to a single metal atom. The term "tridentate" means the three phosphorus atoms on the ligand are bonded to a single metal atom. The P-containing ligand may be a single compound or a mixture of compounds. The P-containing ligand may be selected from the group consisting of a phosphite, a phosphonite, a phosphinite, a phosphine, and a mixed P-containing ligand or a combination of such members. A multidentate P-containing ligand may be represented by Formula I

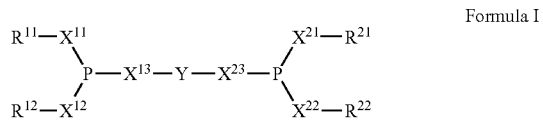

Formula I wherein $X^{11}, X^{12}, X^{13}, X^{21}, X^{22}, X^{23}$ independently represent oxygen or a single bond, $R^{11}, R^{12}$ independently represent identical or different, single or bridged organic radicals, $R^{21}, R^{22}$ independently represent identical or different, single or bridged organic radicals, and Y represents a bridging group.

It is to be understood that Formula I may represent a single compound or a mixture of different compounds having the indicated formula.

In one embodiment, all of the groups $X^{11}$, $X^{12}$, $X^{13}$, $X^{21}$, $X^{22}$, $X^{23}$ may represent oxygen. In such a case, the bridging group Y is joined to phosphite groups. In such a case, the multidentate P-containing ligand represented by Formula I is a phosphite.

In another embodiment, $X^{11}$ and $X^{12}$ may each represent oxygen, and $X^{13}$, a single bond; or $X^{11}$ and $X^{13}$ may each represent oxygen and $X^{12}$, a single bond, so that the phosphorus atom surrounded by $X^{11}$, $X^{12}$, and $X^{13}$ is the central atom of a phosphonite. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$ and $X^{22}$ may each represent oxygen and $X^{23}$, a single bond; or $X^{21}$ and $X^{23}$ may each represent oxygen and $X^{22}$, a single bond, so that the phosphorus atom surrounded by $X^{21}$, $X^{22}$, and $X^{23}$ may be the central atom of a phosphonite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}$, $X^{22}$, and $X^{23}$ may be the central atom of a phosphinite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphite, the multidentate ligand represented by Formula I is a phosphite-phosphonite and is an example of a mixed P-containing ligand. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphonite, the multidentate P-containing ligand represented by Formula I is a phosphonite. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphinite, the multidentate P-containing ligand represented by Formula I is a phosphonite-phosphinite and is an example of a mixed P-containing ligand. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphine, the multidentate P-containing ligand represented by Formula I is a phosphonite-phosphine and is an example of a mixed P-containing ligand.

In another embodiment, $X^{13}$ may represent oxygen and $X^{11}$ and $X^{12}$, each a single bond; or $X^{11}$ may represent oxygen and $X^{12}$ and $X^{13}$, each a single bond, so that the phosphorus atom surrounded by $X^{11}$, $X^{12}$, and $X^{13}$ is the central atom of a phosphinite. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}$, $X^{22}$, and $X^{23}$ may be the central atom of a phosphinite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphite, the multidentate P-containing ligand represented by Formula I is a mixed P-containing ligand. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphinite, the multidentate P-containing ligand represented by Formula I is a phosphinite. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphine, the multidentate P-containing ligand represented by Formula I is a phosphinite-phosphine and is an example of a mixed P-containing ligand.

In another embodiment, $X^{11}$, $X^{12}$, and $X^{13}$ may each represent a single bond, so that the phosphorus atom surrounded by $X^{11}$, $X^{12}$, and $X^{13}$ is the central atom of a phosphine. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphite, the multidentate P-containing ligand represented by Formula I is a phosphite-phosphine and is an example of a mixed P-containing ligand. When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphine, the multidentate P-containing ligand represented by Formula I is a phosphine.

Bridging group Y may be aryl groups substituted, for example, with $C_1$ to $C_4$ hydrocarbyl, or halogen such as fluorine, chlorine, or bromine, or halogenated hydrocarbyl such as trifluoromethyl, or aryl such as phenyl, or unsubstituted aryl groups, for example those with 6 to 20 carbon atoms in the aromatic system, for example 2,2'-biphenyl, 1,1'-bi-2-naphthyl, or pyrocatechol.

Radicals $R^{11}$ and $R^{12}$ may independently represent identical or different organic radicals. $R^{11}$ and $R^{12}$ may be aryl radicals, for example those containing 6 to 10 carbon atoms, which can be unsubstituted or singly or multiply substituted, for example by $C_1$ to $C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{21}$ and $R^{22}$ may independently represent identical or different organic radicals. $R^{21}$ and $R^{22}$ may be aryl radicals, for example those containing 6 to 10 carbon atoms, which can be unsubstituted or singly or multiply substituted, for example by $C_1$ to $C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{11}$ and $R^{12}$ may be single or bridged. Radicals $R^{21}$ and $R^{22}$ may also be single or bridged. Radicals $R^{11}$, $R^{12}$, $R^{21}$, and $R^{22}$ may all be single, or two may be bridged and two single, or all four may be bridged in the manner described.

The P-containing ligand may also be a polymeric ligand composition, as disclosed, for example, in U.S. Pat. Nos. 6,284,865; 6,924,345, or United States Published Patent Application No. 2003/135014. Methods for preparing such polymeric ligand compositions are well known in the art and are disclosed, for example, in the above cited references.

The catalyst may comprise at least one monodentate P-containing ligand selected from the group consisting of a phosphite, a phosphonite, a phosphinite, and a phosphine or a combination of such members. The monodentate P-containing ligand may be added as an additional component of the catalyst when a multidentate P-containing ligand is used, or it may be present, for example, as an impurity from the synthesis of the P-containing ligand, or the monodentate P-containing ligand may be used without a multidentate P-containing ligand. The monodentate P-containing ligand may be represented by Formula II $$P(X^1R^{31})(X^2R^{32})(X^3R^{33})$$  Formula II wherein $X^1$, $X^2$, $X^3$ independently represent oxygen or a single bond, and $R^{31}$, $R^{32}$, $R^{33}$ independently represent identical or different, single or bridged organic radicals.

It is to be understood that Formula II may represent a single compound or a mixture of different compounds having the indicated formula.

In one embodiment, all of the groups $X^1$, $X^2$, and $X^3$ may represent oxygen, so that Formula II represents a phosphite of formula $P(OR^{31})(OR^{32})(OR^{33})$, wherein $R^{31}$, $R^{32}$, and $R^{33}$ have the meanings defined herein.

If one of the groups $X^1$, $X^2$, and $X^3$ represents a single bond and two groups represent oxygen, Formula II represents a phosphonite of formula $P(OR^{31})(OR^{32})(R^{33})$, $P(R^{31})(OR^{32})(OR^{33})$, or $P(OR^{31})(R^{32})(OR^{33})$, wherein $R^{31}$, $R^{32}$, and $R^{33}$ have the meanings defined herein.

If two of the groups $X^1$, $X^2$, and $X^3$ represent single bonds and one group represents oxygen, Formula II represents a phosphinite of formula $P(OR^{31})(R^{32})(R^{33})$ or $P(R^{31})(OR^{32})(R^{33})$ or $P(R^{31})(R^{32})(OR^{33})$, wherein $R^{31}$, $R^{32}$, $R^{33}$ have the meanings defined herein.

The groups $X^1$, $X^2$, $X^3$ may independently represent oxygen or a single bond. If all the groups $X^1$, $X^2$, and $X^3$ represent single bonds, Formula II represents a phosphine of formula $P(R^{31})(R^{32})(R^{33})$, wherein $R^{31}$, $R^{32}$, and $R^{33}$ have the meanings defined herein. Radicals $R^{31}$, $R^{32}$, and $R^{33}$ may independently represent identical or different organic radicals, for example hydrocarbyl radicals comprising 1 to 10 carbon atoms, such as methyl, ethyl, n-propyl, isopropyl, n-butyl, isobutyl, s-butyl, and t-butyl, aryl groups such as phenyl, o-tolyl, m-tolyl, p-tolyl, 1-naphthyl, or 2-naphthyl, or hydrocarbyl radicals comprising 1 to 20 carbon atoms, such as 1,1'-biphenol or 1,1'-binaphthol. The $R^{31}$, $R^{32}$, and $R^{33}$ radicals may be connected to one another directly, meaning not solely via the central phosphorus atom. Alternatively, the $R^{31}$, $R^{32}$, and $R^{33}$ radicals may be not directly connected to one another.

For example, $R^{31}$, $R^{32}$, and $R^{33}$ may be selected from the group composed of phenyl, o-tolyl, m-tolyl, and p-tolyl. As another example, a maximum of two of the $R^{31}$, $R^{32}$, and $R^{33}$ groups may be phenyl. Alternatively, a maximum of two of the $R^{31}$, $R^{32}$, and $R^{33}$ groups may be o-tolyl.

Compounds of Formula IIa, $$(\text{o-tolyl-O-})_w(\text{m-tolyl-O-})_x(\text{p-tolyl-O-})_y(\text{phenyl-O—})_zP$$  Formula IIa may be used as the monodentate P-containing ligand, wherein w, x, y, and z are integers, and the following conditions apply: w+x+y+z=3 and w, z≦2.

Examples of compounds of Formula IVa include (p-tolyl-O-)(phenyl-O—)$_2$P, (m-tolyl-O-)(phenyl-O—)$_2$P, (o-tolyl-O-)(phenyl-O—)$_2$P, (p-tolyl-O-)$_2$(phenyl-O—)P, (m-tolyl-O-)$_2$(phenyl-O—)P, (o-tolyl-O-)$_2$(phenyl-O—)P, (m-tolyl-O-)(p-tolyl-O-)(phenyl-O—)P, (o-tolyl-O-)(p-tolyl-O-)(phenyl-O—)P, (o-tolyl-O-)(m-tolyl-O-)(phenyl-O—)P, (p-tolyl-O—)$_3$P, (m-tolyl-O-)(p-tolyl-O-)$_2$P, (o-tolyl-O-)(p-tolyl-O—)$_2$P, (m-tolyl-O-)$_2$(p-tolyl-O—)P, (o-tolyl-O-)$_2$(p-tolyl-O—)P, (o-tolyl-O-)(m-tolyl-O-)(p-tolyl-O—)P, (m-tolyl-O—)$_3$P, (o-tolyl-O-)(m-tolyl-O—)$_2$P, (o-tolyl-O-)$_2$(m-tolyl-O—)P, or mixtures of such compounds.

Mixtures containing (m-tolyl-O—)$_3$P, (m-tolyl-O-)$_2$(p-tolyl-O—)P, (m-tolyl-O-)(p-tolyl-O—)$_2$P, and (p-tolyl-O—)$_3$P can be obtained, for example, by reacting a mixture containing m-cresol and p-cresol, in particular in a molar ratio of 2:1 as occurs in the distillative processing of crude oil, with a phosphorus trihalide such as phosphorus trichloride.

Additional examples of monodentate P-containing ligands are the phosphites disclosed in U.S. Pat. No. 6,770,770 and referred to herein as phosphites of Formula IIb, $$P(OR^{31})_x(OR^{32})_y(OR^{33})_z(OR^{34})_p$$  Formula IIb wherein $R^{31}$ is an aromatic radical having a $C_1$ to $C_{18}$ alkyl substituent in the o-position relative to the oxygen atom which connects the phosphorus atom to the aromatic system, or having an aromatic substituent in the o-position relative to the oxygen atom which connects the phosphorus atom to the aromatic system, or having an aromatic system fused on in the o-position relative to the oxygen atom which connects the phosphorus atom to the aromatic system;

$R^{32}$ is an aromatic radical having a $C_1$ to $C_{18}$ alkyl substituent in the m-position relative to the oxygen atom which connects the phosphorus atom to the aromatic system, or having an aromatic substituent in the m-position relative to the oxygen atom which connects the phosphorus atom to the aromatic system, or having an aromatic system fused on in the m-position relative to the oxygen atom which connects the phosphorus atom to the aromatic system, where the aromatic radical bears a hydrogen atom in the o-position relative to the oxygen atom which connects the phosphorus atom to the aromatic system;

$R^{33}$ is an aromatic radical having a $C_1$ to $C_{18}$ alkyl substituent in the p-position relative to the oxygen atom which connects the phosphorus atom to the aromatic system, or having an aromatic substituent in the p-position relative to the oxygen atom which connects the phosphorus atom to the aromatic system, where the aromatic radical bears a hydrogen atom in the o-position relative to the oxygen atom which connects the phosphorus atom to the aromatic system;

$R^{34}$ is an aromatic radical which bears substituents other than those defined for $R^{31}$, $R^{32}$, and $R^{33}$ in the o-, m-, and p-position relative to the oxygen atom which connects the phosphorus atom to the aromatic system, where the aromatic radical bears a hydrogen atom in the o-position relative to the oxygen atom which connects the phosphorus atom to the aromatic system;

x is 1 or 2; and y, z, and p independently of one another are 0, 1, or 2, provided that x+y+z+p=3.

Examples of radical $R^{31}$ include o-tolyl, o-ethylphenyl, o-n-propylphenyl, o-isopropylphenyl, o-n-butylphenyl, o-sec-butylphenyl, o-tert-butylphenyl, (o-phenyl)phenyl, or 1-naphthyl groups.

Examples of radical $R^{32}$ include m-tolyl, m-ethylphenyl, m-n-propylphenyl, m-isopropylphenyl, m-n-butylphenyl, m-sec-butylphenyl, m-tert-butylphenyl, (m-phenyl)-phenyl, or 2-naphthyl groups.

Examples of radical $R^{33}$ include p-tolyl, p-ethylphenyl, p-n-propylphenyl, p-isopropylphenyl, p-n-butylphenyl, p-sec-butylphenyl, p-tert-butylphenyl, or (p-phenyl)phenyl groups.

Radical $R^{34}$ may be, for example, phenyl.

The indices x, y, z, and p in compounds of Formula IIb may have the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Examples of phosphites of Formula IIb are those in which p is zero, and $R^{31}$, $R^{32}$, and $R^{33}$ are independently selected from o-isopropylphenyl, m-tolyl, and p-tolyl.

Additional examples of phosphites of Formula IIb are those in which $R^{31}$ is the o-isopropylphenyl radical, $R^{32}$ is the m-tolyl radical, and $R^{33}$ is the p-tolyl radical, with the indices listed in the above table; also those in which $R^{31}$ is the o-tolyl radical, $R^{32}$ is the m-tolyl radical, and $R^{33}$ is the p-tolyl radical, with the indices listed in the table; also those in which $R^{31}$ is the 1-naphthyl radical, $R^{32}$ is the m-tolyl radical, and $R^{33}$ is the p-tolyl radical, with the indices listed in the table; also those in which $R^{31}$ is the o-tolyl radical, $R^{32}$ is the 2-naphthyl radical, and $R^{33}$ is the p-tolyl radical, with the indices listed in the table; and lastly, those in which $R^{31}$ is the o-isopropylphenyl radical, $R^{32}$ is the 2-naphthyl radical, and $R^{33}$ is the p-tolyl radical, with the indices listed in the table; and mixtures of these phosphites.

Phosphites having the Formula IIb can be obtained as follows:

a) phosphorus trihalide is reacted with alcohol selected from the group comprising $R^{31}OH$, $R^{32}OH$, $R^{33}OH$ and $R^{34}OH$ or mixtures thereof to obtain a dihalogenophosphoric acid monoester, b) the aforementioned dihalogenophosphoric acid monoesters are reacted with alcohol selected from the group comprising $R^{31}OH$, $R^{32}OH$, $R^{33}OH$ and $R^{34}OH$ or mixtures thereof to obtain a dihalogenophosphoric acid diester, and c) the aforementioned monohalogenophosphoric acid diester is reacted with alcohol selected from the group comprising $R^{31}OH$, $R^{32}OH$, $R^{33}OH$ and $R^{34}OH$ or mixtures thereof to obtain phosphite having the Formula IIb.

The reaction can be performed in three separate steps. It is also possible to combine two of the three steps, for example a) with b) or b) with c). Alternatively, all steps a), b), and c) can be combined with each other.

Suitable parameters and quantities of the alcohols selected from the group comprising $R^{31}OH$, $R^{32}OH$, $R^{33}OH$ and $R^{34}OH$ or mixtures thereof can be easily determined by conducting a few simple preliminary experiments.

Suitable phosphorus trihalides are in principle all phosphorus trihalides in which preferable Cl, Br, I, particularly Cl is used as the halide, as well as mixtures thereof. It is also possible to use mixtures of different equally or differently halogen-substituted phosphines as the phosphorus trihalide, for example $PCl_3$. Further details regarding the reaction conditions during the production of phosphites of Formula IIb and regarding the treatment are disclosed in DE-A 199 53 058.

Phosphites of Formula IIb can also be used as a mixture of different phosphites as ligand. Such a mixture can be formed, for example, in the preparation of phosphites of Formula IIb.

In one embodiment of the process of the invention, the phosphorus-containing ligand of the catalyst and/or the free phosphorus-containing ligand is selected from at least one multidentate P-containing ligand selected from the group consisting of a phosphite, a phosphonite, a phosphinite, a phosphine, and a mixed P-containing ligand or a combination of such members, and at least one monodentate P-containing ligand selected from tritolyl phosphite and the phosphites of Formula IIb wherein $R^{31}$, $R^{32}$, and $R^{33}$ are independently selected from o-isopropylphenyl, m-tolyl, and p-tolyl, $R^{34}$ is phenyl, x is 1 or 2, and y, z, and p are independently 0, 1, or 2, provided that x+y+z+p=3; and mixtures thereof.

Examples of multidentate P-containing ligands include the following:

1) the compounds of Formula I, II, III, IV, and V disclosed in U.S. Pat. No. 5,723,641;
2) the compounds of Formula I, II, III, IV, V, VI, and VII disclosed in U.S. Pat. No. 5,512,696, for example the compounds used in Examples 1 through 31 therein;
3) the compounds of Formula I, II, III, IV, V, VI, VII, VIII, IX, X, XI, XII, XIII, XIV, and XV disclosed in U.S. Pat. No. 5,821,378, for example the compounds used in Examples 1 through 73 therein;
4) the compounds of Formula I, II, III, IV, V, and VI disclosed in U.S. Pat. No. 5,512,695, for example the compounds used in Examples 1 through 6 therein;
5) the compounds of Formula I, II, III, IV, V, VI, VII, VIII, IX, X, XI, XII, XIII, and XIV disclosed in U.S. Pat. No. 5,981,772, for example the compounds used in Examples 1 through 66 therein;
6) the compounds disclosed in U.S. Pat. No. 6,127,567, for example the compounds used in Examples 1 through 29 therein;
7) the compounds of Formula I, II, III, IV, V, VI, VII, VIII, IX, and X disclosed in U.S. Pat. No. 6,020,516, for example the compounds used in Examples 1 through 33 therein;
8) the compounds disclosed in U.S. Pat. No. 5,959,135, for example the compounds used in Examples 1 through 13 therein;
9) the compounds of Formula I, II, and III disclosed in U.S. Pat. No. 5,847,191;
10) the compounds disclosed in U.S. Pat. No. 5,523,453, for example the compounds of Formula 1, 2, 3, 4, 5, 6, 7, 8, 9, 10, 11, 12, 13, 14, 15, 16, 17, 18, 19, 20, and 21 therein;
11) the compounds disclosed in U.S. Pat. No. 5,693,843, for example the compounds of Formula I, II, III, IV, V, VI, VII, VIII, IX, X, XI, XII, and XIII, for example the compounds used in Examples 1 through 20 therein;
12) the compounds of Formula V, VI, VII, VIII, IX, X, XI, XII, XIII, XIV, XV, XVI, XVII, XVIII, XIX, XX, XXI, XXII, XXIII, XXIV, XXV, and XXVI disclosed in U.S. Pat. No. 6,893,996;
13) the compounds disclosed in published patent application WO 01/14392, for example the compounds illustrated in Formula V, VI, VII, VIII, IX, X, XI, XII, XII, XIV, XV, XVI, XVII, XXI, XXII, and XXIII therein;
14) the chelating compounds disclosed in U.S. Pat. No. 6,242,633, for example the compounds of Formula If, Ig, and Ih;
15) the compounds disclosed in U.S. Pat. No. 6,521,778, for example the compounds of Formula I, Ia, Ib, and Ic, for example the compounds referred to as Ligand I and II;

16) the compounds disclosed in published patent application WO 02/13964, for example the compounds of Formula Ia, Ib, Ic, Id, Ie, If, Ig, Ih, Ii, Ij, and Ik, for example the compounds referred to as Ligand 1, 2, 3, 4, 5, and 6;
17) the compounds disclosed in German Patent Application DE 100 460 25;
18) the chelating compounds disclosed in U.S. Pat. No. 7,022,866, for example the compounds of Formula 1 and 2, for example the compounds referred to as Ligand 1 and 2;
19) the compounds disclosed in United States Published Patent Application No. 2005/0090677, for example the compounds of Formula 1, 1a, 1b, 1c, 1d, 1e, 1f, 1g, 1h, 1i, 1j, 1k, 1l, 1m, 1n, 1o, 2, and 3;
20) the compounds disclosed in United States Published Patent Application No. 2005/0090678, for example the compounds of Formula 1 and 2, for example the compounds referred to as Ligand 1, 2, 3, 4, 5, and 6;
21) the compounds disclosed in published patent application WO 2005/042547, for example the compounds of Formula 1, 1a, 1b, 1c, 1d, 1e, 1f, 1g, 1h, 1i, 1j, 1k, 1l, 1m, 1n, 1o, 2, 3, 4, 5, and 6, for example the compounds referred to as Ligand 1, 2, 3, and 4;
22) the chelating compounds disclosed in U.S. Pat. No. 6,169,198, for example the compounds of Formula I;
23) the compounds disclosed in U.S. Pat. No. 6,660,877, for example the compounds of Formula I, II, and III, for example the compounds used in Examples 1 through 27 therein;
24) the compounds disclosed in U.S. Pat. No. 6,197,992, for example the compounds of Ligand A and B: and
25) the compounds disclosed in U.S. Pat. No. 6,242,633, for example the compounds of Formula I, Ia, Ib, Ic, Id, Ie, If, Ig, and Ih.

These references also disclose methods for preparing multidentate ligands of Formula I.

Additional examples of ligands which, in combination with nickel, form highly active catalysts for the hydrocyanation of 1,3-butadiene or 3-pentenenitrile and the isomerization of 2-methyl-3-butenenitrile to 3-pentenenitrile are bidentate phosphite ligands are of the following structural formulae:

Formula IIIa

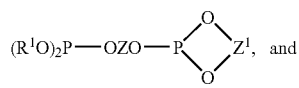

Formula IIIb

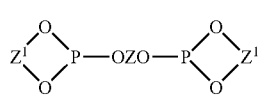

Formula IIIc wherein in IIIa, IIIb, and IIIc $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

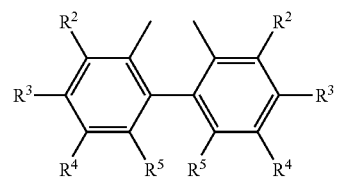

IV

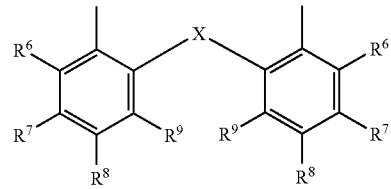

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or CH($R^{10}$);
$R^{10}$ is H or $C_1$ to $C_{12}$ alkyl;

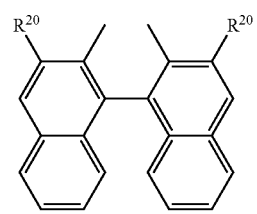

VI

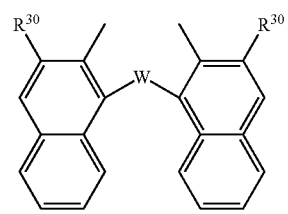

VII and wherein
$R^{20}$ and $R^{30}$ are independently selected from the group consisting of H, $C_1$ to $C_{12}$ alkyl, and $C_1$ to $C_{12}$ alkoxy; and $CO_2R^{13}$,
$R^{13}$ is $C_1$ to $C_{12}$ alkyl or $C_6$ to $C_{10}$ aryl, unsubstituted or substituted with $C_1$ to $C_4$ alkyl;
W is O, S, or CH($R^{14}$);
$R^{14}$ is H or $C_1$ to $C_{12}$ alkyl;

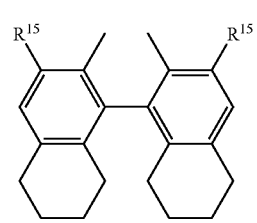

VIII wherein

R[15] is selected from the group consisting of H, $C_1$ to $C_{12}$ alkyl, and $C_1$ to $C_{12}$ alkoxy and $CO_2R^{16}$;

R[16] is $C_1$ to $C_{12}$ alkyl or $C_6$ to $C_{10}$ aryl, unsubstituted or substituted with $C_1$ to $C_4$ alkyl.

In the structural formulae IIIa, IIIb, IIIc, and IV through VIII, the $C_1$ to $C_{12}$ alkyl, and $C_1$ to $C_{12}$ alkoxy groups may be straight chain or branched.

It is to be understood that structural formulae IIIa, IIIb, and IIIc may represent a single compound or a mixture of different compounds having the indicated formulae.

Examples of bidentate phosphite ligands that are useful in the present process include those having the formulae IX to XXXII, shown below wherein for each formula, R[17] is selected from the group consisting of methyl, ethyl or isopropyl, and R[18] and R[19] are independently selected from H or methyl:

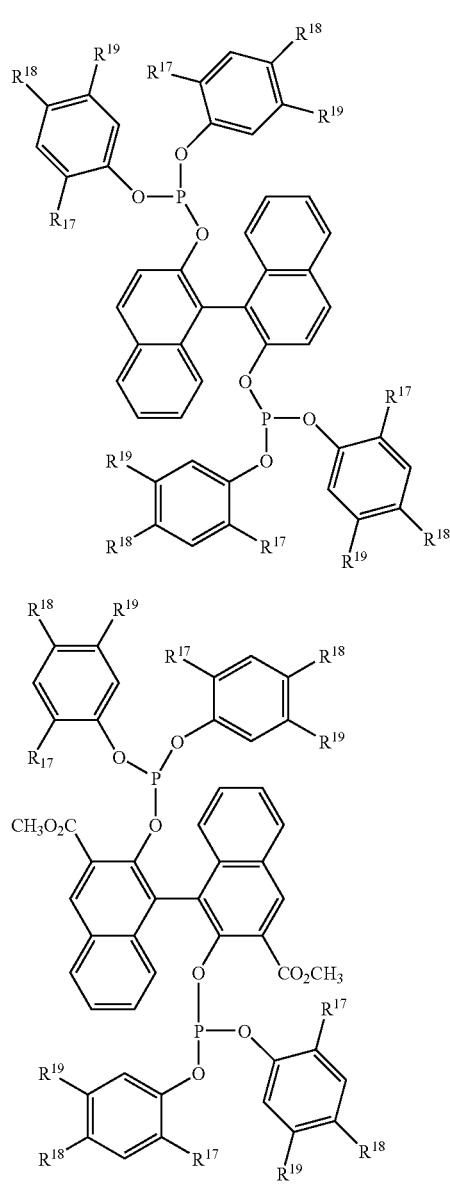

IX

X

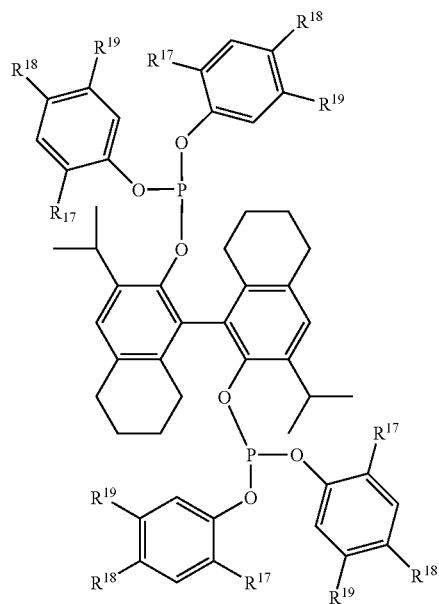

XI

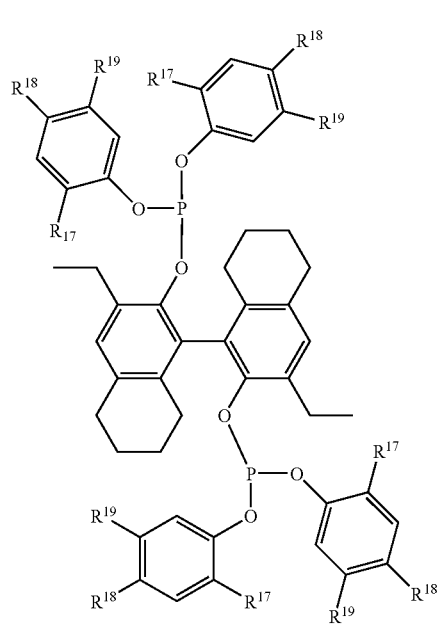

XII

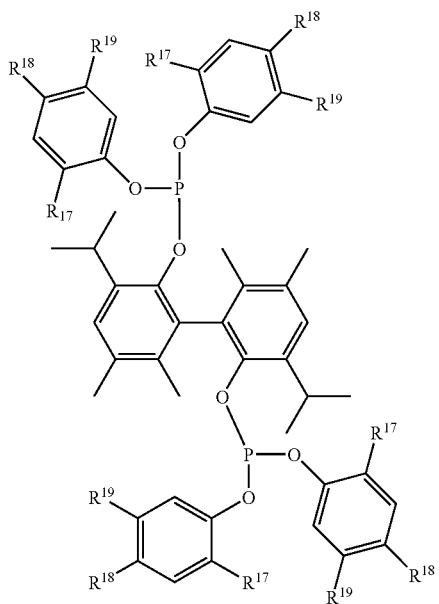
XIII
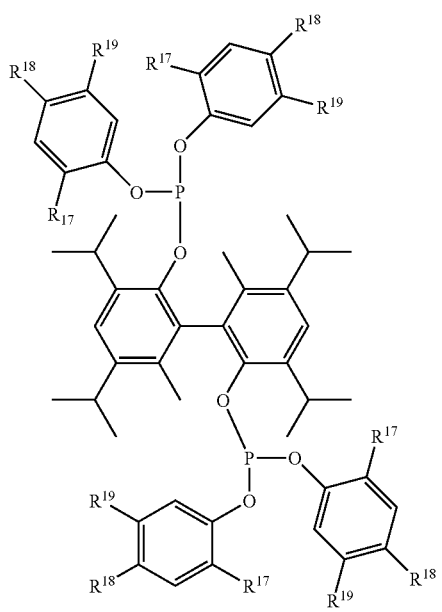
XV
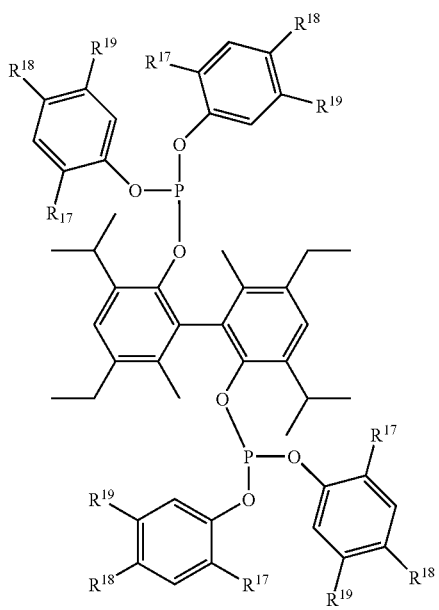
XIV
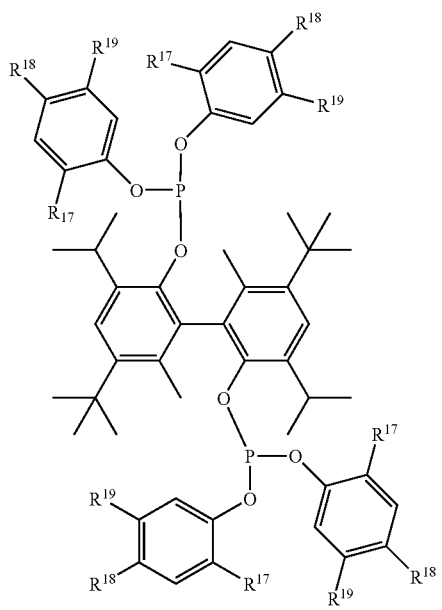
XVI

XVII
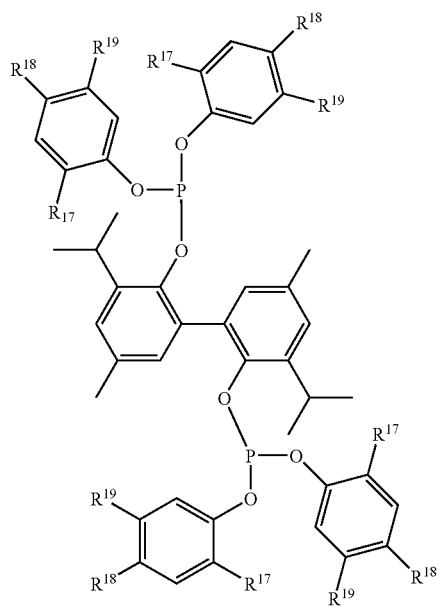
XVIII
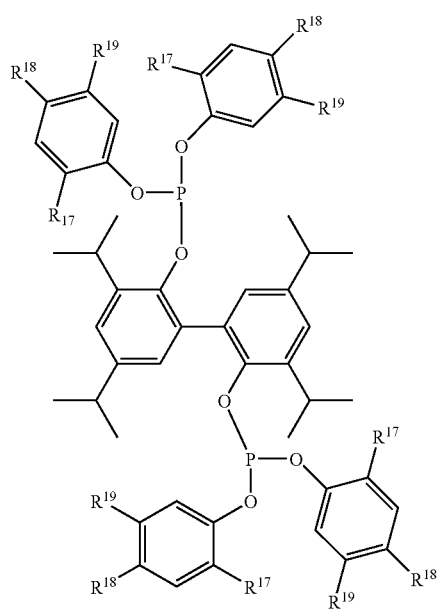
XIX
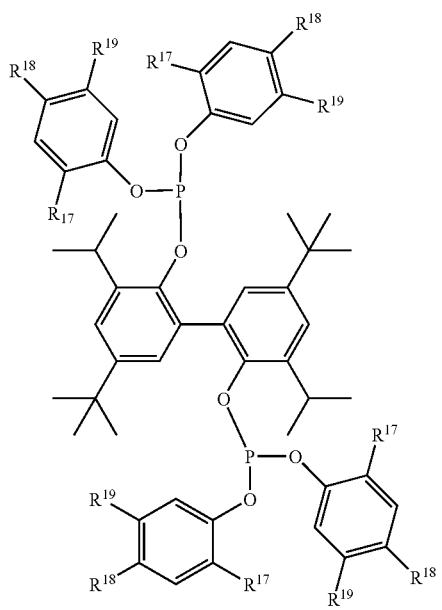
XX
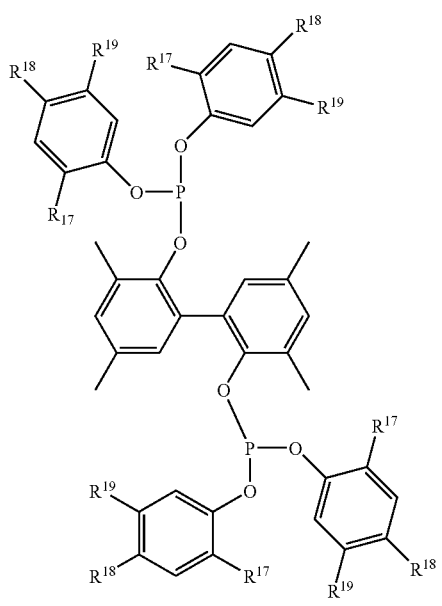

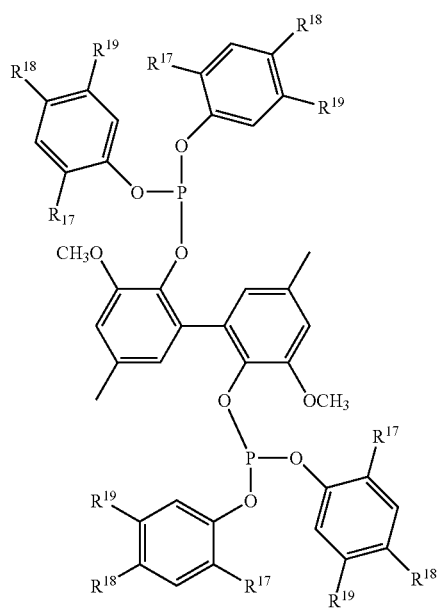
XXI
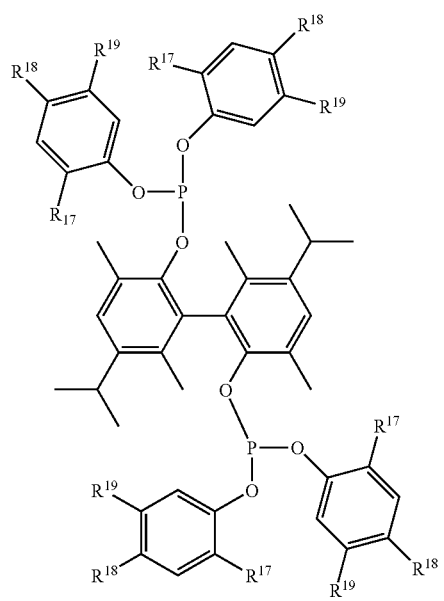
XXIII
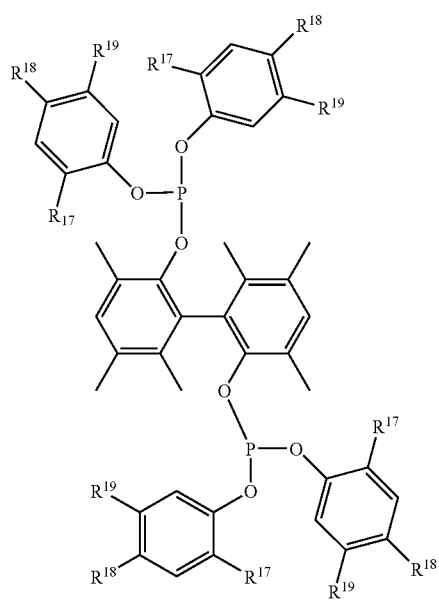
XXII
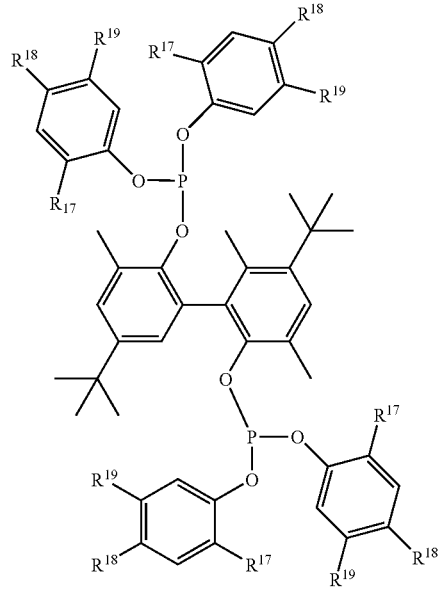
XXIV

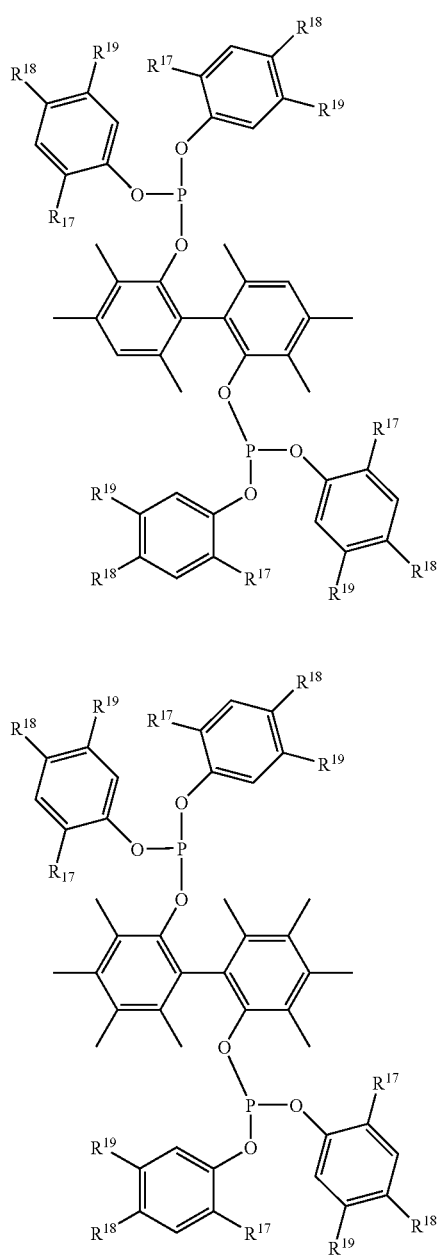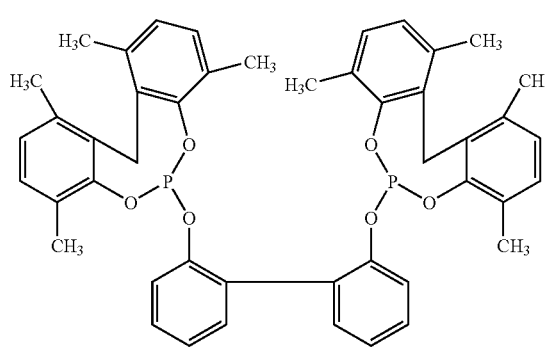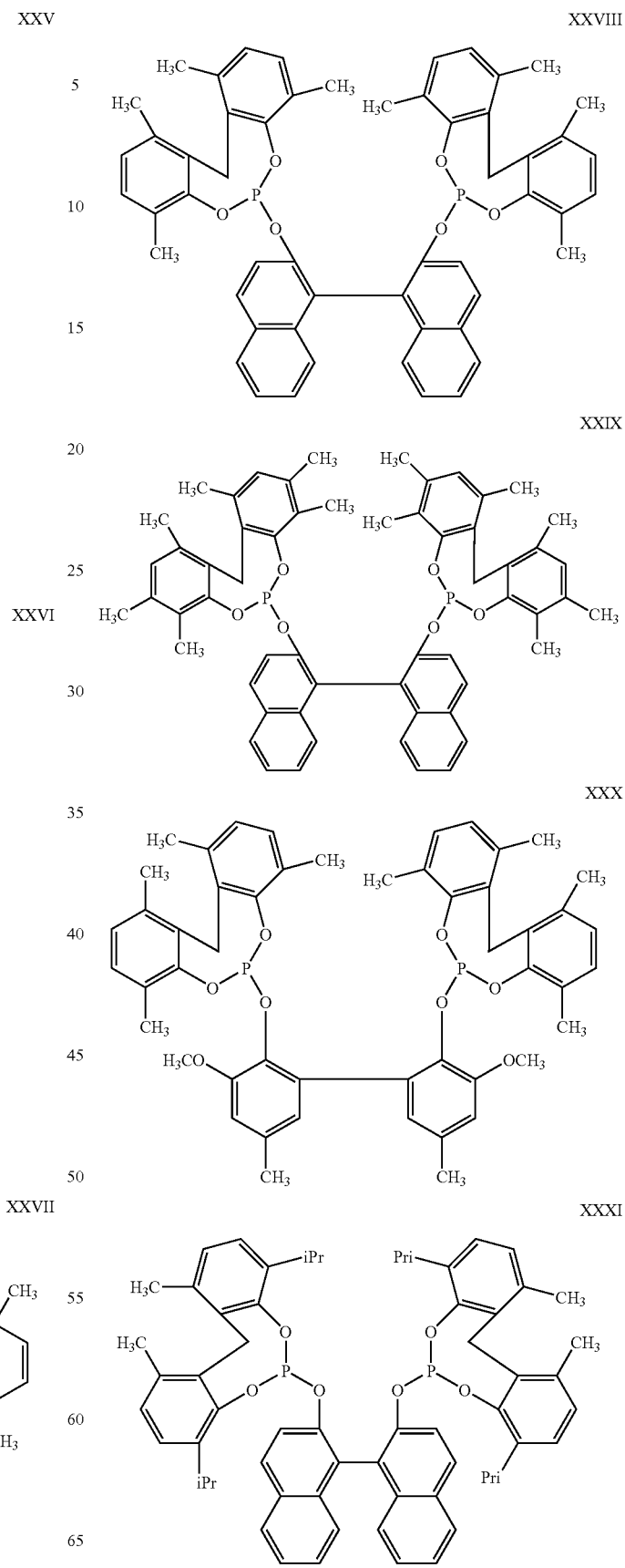

-continued

XXXII

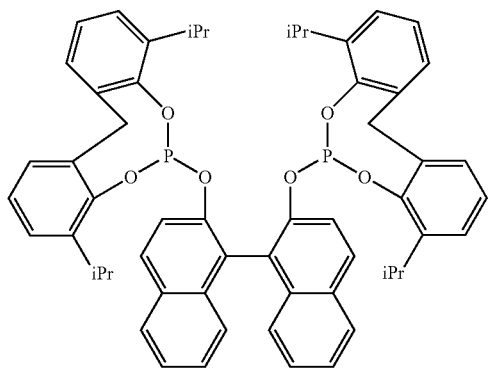

Additional examples of bidentate phosphite ligands that are useful in the present process include a ligand selected from a member of the group represented by Formulas XXXIII and XXXIV, in which all like reference characters have the same meaning, except as further explicitly limited:

Formula XXXIII

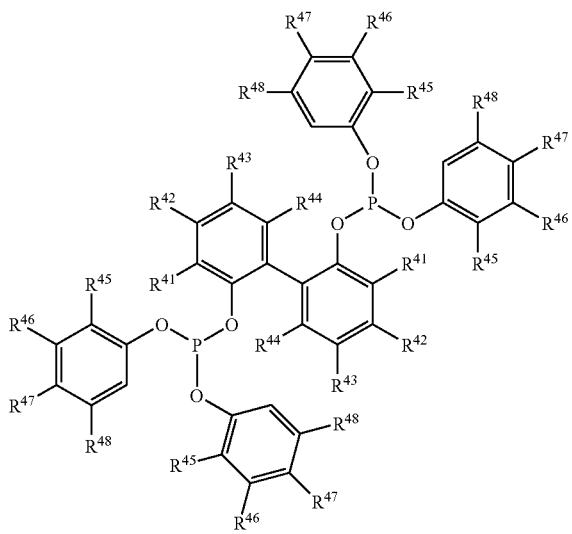

Formula XXXIV

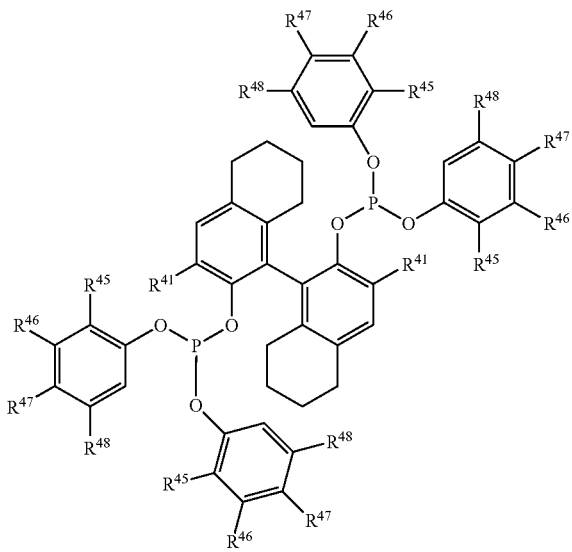

wherein $R^{41}$ and $R^{45}$ are independently selected from the group consisting of $C_1$ to $C_5$ hydrocarbyl, and each of $R^{42}$, $R^{43}$ $R^{44}$ $R^{46}$, $R^{47}$ and $R^{48}$ is independently selected from the group consisting of H and $C_1$ to $C_4$ hydrocarbyl.

For example, the bidentate phosphite ligand can be selected from a member of the group represented by Formula XXXIII and Formula XXXIV, wherein
  $R^{41}$ is methyl, ethyl, isopropyl or cyclopentyl;
  $R^{42}$ is H or methyl;
  $R^{43}$ is H or a $C_1$ to $C_4$ hydrocarbyl;
  $R^{44}$ is H or methyl;
  $R^{45}$ is methyl, ethyl or isopropyl; and
  $R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula XXXIII, wherein
  $R^{41}$, $R^{44}$, and $R^{45}$ are methyl;
  $R^{42}$, $R^{46}$, $R^{47}$ and $R^{48}$ are H; and
  $R^{43}$ is a $C_1$ to $C_4$ hydrocarbyl;
or
  $R^{41}$ is isopropyl;
  $R^{42}$ is H;
  $R^{43}$ is a $C_1$ to $C_4$ hydrocarbyl;
  $R^{44}$ is H or methyl;
  $R^{45}$ is methyl or ethyl;
  $R^{46}$ and $R^{48}$ are H or methyl; and
  $R^{47}$ is H, methyl or tertiary-butyl;
or the bidentate phosphite ligand can be selected from a member of the group represented by Formula XXXIV, wherein
  $R^{41}$ is isopropyl or cyclopentyl;
  $R^{45}$ is methyl or isopropyl; and
  $R^{46}$, $R^{47}$, and $R^{48}$ are H.

As yet another example, the bidentate phosphite ligand can be represented by Formula XXXIII, wherein $R^{41}$ is isopropyl; $R^{42}$, $R^{46}$, and $R^{48}$ are H; and $R^{43}$, $R^{44}$, $R^{45}$, and $R^{47}$ are methyl.

It is to be understood that the formulas above are two-dimensional representations of three-dimensional molecules and that rotation about chemical bonds can occur in the molecules to give configurations differing from those shown. For example, rotation about the carbon-carbon bond between the 2- and 2'-positions of the biphenyl and octahydrobinaphthyl bridging groups of Formula XXXIII and Formula XXXIV, respectively, can bring the two phosphorus atoms of each Formula in closer proximity to one another and can allow the phosphite ligand to bind to nickel in a bidentate fashion.

A multidentate P-containing ligand may be suitable for use in the process of the invention if, as part of a catalyst composition comprising a zero-valent nickel and the multidentate P-containing ligand, it can be used within a temperature range of about 80° C. to about 140° C. to produce a reaction mixture comprising 3PN and 2M3BN from a HCN-containing feed and a BD-containing feed. The multidentate P-containing ligand is suitable for use in the process of the invention in the case where the 2M3BN concentration of the reaction mixture comprising 3PN and 2M3BN can be maintained below about 15 weight percent of the total mass of the reaction mixture, for example at or below about 10 weight percent of the total mass of the reaction mixture, and the HCN conversion is about 95% or more. A catalyst composition, comprising a P-containing ligand suitable for the process of the invention, may lack sufficient 3PN selectivity in BD hydrocyanation to produce a reaction mixture comprising 3PN and 2M3BN wherein the 2M3BN concentration is maintained below about 15 weight percent of the total mass of the reaction mixture. However, when used to hydrocyanate BD and to isomerize 2M3BN to 3PN concurrently in the same reaction zone, with a sufficient residence time, a catalyst composition comprising a suitable P-containing ligand can produce a reaction mixture comprising 3PN and 2M3BN wherein the 2M3BN concentration is maintained below about 15 weight percent of the total mass of the reaction mixture. For the concurrent BD hydrocyanation/ 2M3BN isomerization process with a suitable multidentate P-containing ligand, the molar ratio of the HCN in the feed to the BD in the feed is in the range of about 0.90:1.00 to about 1.04:1.00. The molar ratio of the zero-valent nickel in the feed to the BD in the feed is in the range of about 0.00005:1.00 to about 0.0050:1.00. The molar ratio of multidentate P-containing ligand to zero-valent nickel is in the range of about 1/1 to about 6/1. Solvent, HCN, preparation of the catalyst composition, reactor startup, and other operational information are as described for the process of the invention in other sections of this document.

The P-containing ligands useful in the present invention may be prepared by any suitable synthetic means known in the art. For example, in general the multidentate P-containing ligands may be synthesized analogously to the method described in U.S. Pat. Nos. 6,171,996 and 5,512,696, both of which are incorporated herein by reference. For example, the reaction of two equivalents of an ortho-substituted phenol with phosphorus trichloride gives the corresponding phosphorochloridite. The reaction of the phosphorochloridite with the desired substituted biphenol or octahydrobinaphthol in the presence of triethylamine gives the bidentate phosphite ligand. The crude bidentate phosphite ligand can be worked up by the process described in U.S. Pat. No. 6,069,267, which is incorporated herein by reference. As disclosed therein, the bidentate phosphite ligand product mixture can typically contain the desired product in about 70% to about 90% selectivity, with other phosphite by-products such as monodentate phosphites making up the balance of the product mixture.

The multidentate P-containing ligand itself or mixtures of the multidentate P-containing ligand and at least one monodentate P-containing ligand are suitable for use with the present invention.

The catalyst compositions employed for this process should ideally be substantially free of carbon monoxide, oxygen, and water and may be preformed or prepared in situ according to techniques well known in the art. For example, the catalyst composition may be formed by contacting the bidentate phosphite ligand with a zero-valent nickel compound having ligands easily displace by organophosphite ligands, such as $Ni(COD)_2$, $Ni[P(O-o-C_6H_4CH_3)_3]_3$, and $Ni[P(O-o-C_6H_4CH_3)_3]_2(C_2H_4)$, all of which are well known in the art, wherein 1,5-cyclooctadiene (COD), tris(ortho-tolyl)phosphite $[P(O-o-C_6H_4CH_3)_3]$, and ethylene $(C_2H_4)$ are the easily displaced ligands. Elemental nickel, preferably nickel powder, when combined with a halogenated catalyst, as described in U.S. Pat. No. 3,903,120, is also a suitable source of zero-valent nickel. Alternatively, divalent nickel compounds can be combined with a reducing agent, to serve as a source of zero-valent nickel in the reaction, in the presence of the bidentate phosphite ligands. Suitable divalent nickel compounds include compounds of the formula $NiZ_2$ where Z is halide, carboxylate, or acetylacetonate. Suitable reducing agents include metal borohydrides, metal aluminum hydrides, metal alkyls, Li, Na, K, Zn, Fe or $H_2$. See, for example, U.S. Pat. No. 6,893,996, which is incorporated herein by reference. In the catalyst composition, the bidentate phosphite ligand may be present in excess of what can theoretically be coordinated to the nickel at a given time.

The catalyst composition may be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst composition.

The HCN-containing feed, the BD-containing feed, and the catalyst composition are contacted in a reaction zone which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

The reaction temperature is typically maintained within the range of about 80° C. to about 140° C., for example within the range of about 100° C. to about 130° C. Generally, the reaction pressure should be sufficient to maintain the reagents in the liquid state, with such pressure at least, in part, a function of the amount of unreacted BD present in the reaction mixture. Though the invention is not limited by an upper limit of pressure, for practical purposes the pressure generally ranges from about 15 psia to about 300 psia (about 103 kPa to about 2068 kPa).

HCN, substantially free of carbon monoxide, oxygen, ammonia, and water can be introduced to the reaction as a vapor, liquid, or mixtures thereof. As an alternative, a cyanohydrin can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00. This range of molar ratios can be advantageous over those with a significantly larger excess of BD to HCN in that there can be less unreacted BD to recover and recycle to the process, and yield losses to MGN and to BD dimers, oligomers, and related species can be reduced.

The molar ratio of the zero-valent nickel in the feed to the BD in the feed is in the range of about 0.00005:1.00 to about 0.0050:1.00, for example in the range about 0.0001:1.00 to about 0.0010:1.00.

The residence time in the reaction zone (for example, the time necessary for the combined feeds to displace one reactor volume in a CSTR) is typically determined by the desire to maintain the 2M3BN concentration below about 15 weight percent of the total mass of the reaction mixture, for example at or below about 10 weight percent of the total mass of the reaction mixture, and is also related to the catalyst concentration and reaction temperature. Generally residence times will be in the range of about 0.5 to about 15 hours, for example in the range of about 1 to about 10 hours.

The reaction mixture comprising 3PN and 2M3BN is distilled in an apparatus for distillation to obtain a first stream comprising BD, a second stream comprising 3PN, 2M3BN, (Z)-2M2BN, and optionally BD, and a third stream comprising the catalyst composition. The distillation can be performed in any suitable equipment known to one skilled in the art. Examples of conventional equipment suitable for this distillation include sieve tray columns, bubble tray columns, columns with regular packing, random packed columns or single-stage evaporators, such as falling film evaporators, thin-film evaporators, flash distillation evaporators, multiphase helical coil evaporators, natural circulation evaporators or forced circulation flash evaporators. The distillation can be performed in one or more pieces of equipment.

In one embodiment, the distillation apparatus comprises at least one distillation column. The distillation column can be provided with a structured packing section above the feed location to prevent catalyst entrainment in the distillate and to generate an appropriate number of stages of separation. The reaction mixture is distilled in at least one distillation column at less than one atmosphere pressure and with a base temperature of less than about 140° C., for example less than about 130° C., or for example less than about 120° C. The base temperature is chosen in part to maintain the thermal stability of the catalyst composition.

In the distillation of the reaction mixture comprising 3PN and 2M3BN, a first stream comprising BD is obtained. The first stream contains about 0 percent to about 50 percent by weight, for example about 0 percent to about 20 percent by weight, or for example about 0 percent to about 40 percent by weight BD. The first stream may optionally contain about 0 percent to about 50 percent by weight, for example about 0 percent to about 20 percent by weight, or for example about 0 percent to about 40 percent by weight butene. As a result of the distillation, the first stream is enriched in BD and depleted in 3PN and 2M3BN, as compared to the reaction mixture. The first stream is also depleted in the catalyst composition, as compared to the reaction mixture.

The first stream may be obtained as a vapor stream in at least one condenser at the top of the distillation column, with pentenenitriles being condensed from the vapor stream of the distillation column at least partially in at least one condenser and being returned to the distillation column at least partially in the liquid state as a stream containing pentenenitriles as well as BD and butene.

Alternatively, the distillation can be performed with a direct contact condenser so that the condensation is performed in a column section, which is for example provided with a structured column packing, a collecting cup beneath this packing, a liquid discharge feature from the collecting cup, a transfer pumping circuit which is connected to the liquid discharge feature, with a pump and heat exchanger as well as at least one apparatus for adding the transfer-pumped liquid flow to the packing above the collecting cup.

In the distillation of the reaction mixture comprising 3PN and 2M3BN, a second stream comprising 3PN, 2M3BN, (Z)-2M2BN, and optionally BD is obtained. The second stream contains about 50 percent by weight to about 85 percent by weight 3PN and 4PN together, for example about 60 percent by weight to about 85 percent by weight 3PN and 4PN together; about 5 percent by weight to about 40 percent by weight 2M3BN, for example about 5 percent by weight to about 30 percent by weight 2M3BN; and about 0 percent by weight to about 3 percent by weight (Z)-2M2BN. The second stream also optionally contains BD and butene, for example less than about 4 percent by weight each of BD and butene. As a result of the distillation, the second stream is depleted in BD and enriched in 3PN and 2M3BN, as compared to the reaction mixture. The second stream is also depleted in the catalyst composition, as compared to the reaction mixture. Depending on the conditions used to operate the distillation column and the desired degree of separation, the second stream may be obtained as a vapor or liquid stream, and may be obtained from a variety of withdrawal points, for example from the top of the column, near the top of the column, or as a side-draw stream, for example at a position in the distillation column below the feed point of the reaction mixture.

In the distillation of the reaction mixture comprising 3PN and 2M3BN, a third stream comprising the catalyst composition is also obtained. The third stream can be obtained as a bottom product and contains about 30 percent by weight to about 70 percent by weight 3PN and up to a third as much 2M3BN, for example about 10 percent by weight to about 23 percent by weight 2M3BN. The remainder of the stream is comprised of dinitriles and the catalyst composition, optionally including degradation products of the catalyst composition. As a result of the distillation, the third stream is enriched in the catalyst composition and depleted in BD, in 3PN, and in 2M3BN as compared to the reaction mixture. In one embodiment of the process, at least a portion of the third stream can be returned to the reaction zone. Alternatively, at least a portion of the third stream can be introduced into a liquid-liquid extraction process to recover the catalyst composition, as disclosed for example in U.S. Pat. No. 6,936,171, which is incorporated herein by reference, and subsequently, the recovered catalyst composition can be returned to the reaction zone if so desired.

The second stream comprising 3PN, 2M3BN, (Z)-2M2BN, and optionally BD is distilled in an apparatus for distillation to obtain a fourth stream comprising BD, a fifth stream comprising 2M3BN, (Z)-2M2BN, and optionally BD, and a sixth stream comprising 3PN. The distillation can be performed in any suitable equipment known to one skilled in the art. Examples of conventional equipment suitable for this distillation include sieve tray columns, bubble tray columns, columns with regular packing, random packed columns or single-stage evaporators, such as falling film evaporators, thin-film evaporators, flash distillation evaporators, multiphase helical coil evaporators, natural circulation evaporators or forced circulation flash evaporators.

The distillation column may contain conventional trays or structured packings sufficient to generate an appropriate number of separation stages. The second stream is distilled in at least one distillation column at or above one atmosphere pressure, for example in the range of one to three atmospheres pressure.

In the distillation of the second stream comprising 3PN, 2M3BN, (Z)-2M2BN, and optionally BD, a fourth stream comprising BD is obtained. The fourth stream contains about 0 percent by weight to about 50 percent by weight, for example about 0 percent by weight to about 20 percent by weight, or for example about 0 percent by weight to about 40 percent by weight BD. The fourth stream optionally contains about 0 percent by weight to about 50 percent by weight, for example about 0 percent by weight to about 20 percent by weight, or for example about 0 percent by weight to about 40 percent by weight butene. As a result of the distillation, the fourth stream is enriched in BD and depleted in 3PN, 2M3BN, and (Z)-2M2BN, as compared to the second stream.

The fourth stream may be obtained as a vapor stream in at least one condenser at the top of the distillation column, with pentenenitriles being condensed off from the vapor stream of the distillation column at least partially in at least one condenser and being returned to the distillation column at least partially in the liquid state as a stream containing pentenenitriles as well as BD and butene.

Alternatively, the distillation can be performed with a direct contact condenser so that the condensation is performed in a column section, which is for example provided with a structured column packing, a collecting cup beneath this packing, a liquid discharge feature from the collecting cup, a transfer pumping circuit which is connected to the liquid discharge feature, with a pump and heat exchanger as well as at least one apparatus for adding the transfer-pumped liquid flow to the packing above the collecting cup.

In the distillation of the second stream comprising 3PN, 2M3BN, (Z)-2M2BN, and optionally BD, a fifth stream comprising 2M3BN, (Z)-2M2BN, and optionally BD is obtained. The fifth stream contains about 40 percent by weight to about 80 percent by weight 2M3BN, for example about 45 percent by weight to about 75 percent by weight 2M3BN, and about 0 percent by weight to about 20 percent by weight (Z)-2M2BN. The fifth stream also contains about 0 percent by weight to about 10 percent by weight 3PN and 4PN together. Optionally, the fifth stream also contains about 0 percent by weight to about 12 percent by weight each of BD and butene. As a result of the distillation, the fifth stream is enriched in 2M3BN and (Z)-2M2BN, as compared to the second stream. The fifth stream is depleted in 3PN, as compared to the second stream. Depending on the conditions used to operate the distillation column and the desired degree of separation, the fifth stream may be obtained as a vapor or liquid stream, and may be obtained from a variety of withdrawal points, for example from the top of the column, near the top of the column, or as a side-draw stream.

In the distillation of the second stream, a sixth stream comprising 3PN is also obtained. The sixth stream can be obtained as a bottom product and contains less than about 2.0 percent by weight, or for example less than about 1.0 percent by weight, or for example less than about 0.5 percent by weight, or for example less than about 0.2 percent by weight 2M3BN. As a result of the distillation, the sixth stream is enriched in 3PN as compared to the second stream. Also as a result of the distillation, the sixth stream is depleted in 2M3BN and (Z)-2M2BN as compared to the second stream. In one embodiment of the process, at least a portion of the sixth stream is hydrocyanated to produce a dinitrile product comprising ADN.

As is understood by one skilled in the art, the selection of the feed point in the column is related to the degree of separation desired for the material to be distilled. The second stream can be fed below the rectification section of the column in order to achieve the desired separation with a minimal amount of 3PN present in the fifth stream. The second stream can be fed above the stripping section of the column in order to achieve the desired separation with a minimal amount of 2M3BN present in the sixth stream.

The fifth stream comprising 2M3BN, (Z)-2M2BN, and optionally BD is distilled in at least one apparatus for distillation to obtain a seventh stream comprising BD, an eighth stream comprising (Z)-2M2BN, and a ninth stream comprising 2M3BN. The distillation can be performed in any suitable equipment known to one skilled in the art. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators. The distillation can be performed in one or more pieces of equipment.

The distillation columns may contain conventional trays or structured packings sufficient to generate an appropriate number of stages of separation. The fifth stream is distilled in at least one distillation column. The fifth stream may be introduced into the rectifying section of the column.

In the distillation of the fifth stream comprising 2M3BN, (Z)-2M2BN, and optionally BD, a seventh stream comprising BD is obtained. This stream contains about 0 to about 50 percent by weight, for example about 0 to about 20 percent by weight, or for example about 0 to about 40 percent by weight BD. The fifth stream may also optionally contain about 0 percent by weight to about 50 percent by weight butene, for example from about 0 to about 20 percent by weight butene, or for example from about 0 to about 40 percent by weight butene. As a result of the distillation, the seventh stream is enriched in BD and depleted in 2M3BN and (Z)-2M2BN, as compared to the fifth stream.

The seventh stream may be obtained as a vapor stream in at least one condenser at the top of the distillation column, with the 2M3BN and 2M2BN being condensed from the vapor stream of the distillation column at least partially in at least one condenser and being returned to the distillation column at least partially in the liquid state as a stream containing (Z)-2M2BN as well as BD. In another embodiment of the process, the seventh stream is obtained as a vapor stream and is combined with the fourth stream, which is also obtained as a vapor stream. The combined streams are condensed in at least one condenser, with the 2M3BN and 2M2BN being condensed from the vapor stream and being returned to the distillation column from which the fourth stream was obtained at least partially in the liquid state.

Alternatively, the distillation can be performed with a direct contact condenser so that the condensation is performed in a column section, which is for example provided with a structured column packing, a collecting cup beneath this packing, a liquid discharge feature from the collecting cup, a transfer pumping circuit which is connected to the liquid discharge feature, with a pump and heat exchanger as well as at least one apparatus for adding the transfer-pumped liquid flow to the packing above the collecting cup.

In the distillation of the fifth stream comprising 2M3BN, (Z)-2M2BN, and optionally BD, an eighth stream comprising (Z)-2M2BN is obtained. The eighth stream contains about 10 percent by weight to about 80 percent by weight, for example about 10 percent by weight to about 50 percent by weight, or about 10 percent by weight to about 30 percent by weight (Z)-2M2BN. The eighth stream also contains about 10 percent by weight to about 50 percent by weight, for example about 15 percent by weight to about 45 percent by weight, or for example about 20 percent by weight to about 40 percent by weight 2M3BN. As a result of the distillation, the eighth stream is enriched in (Z)-2M2BN and depleted in 2M3BN, as compared to the fifth stream. Depending on the conditions used to operate the distillation column and the desired degree of separation, the eighth stream may be obtained as a vapor or a liquid stream, and may be obtained from a variety of withdrawal points, for example from the top of the column, near the top of the column, or as a side-draw stream. If desired, the feed may be located above a stripping section to enhance removal of impurities, for example 4-vinyl-1-cyclohexene.

In the distillation of the fifth stream, a ninth stream comprising 2M3BN is also obtained. The ninth stream can be obtained as a bottom product and contains about 40 percent by weight to about 80 percent by weight, for example about 50 percent by weight to about 75 percent by weight 2M3BN. The ninth stream also contains about 0 percent by weight to about 20 percent by weight (Z)-2M2BN, for example about 1 percent by weight to about 15 percent by weight (Z)-2M2BN. As a result of the distillation, the ninth stream is enriched in 2M3BN and depleted in (Z)-2M2BN, as compared to the fifth stream.

FIG. 1 schematically illustrates one embodiment of the processes of the invention. In FIG. 1, each distillation column is shown as having a feed point in the middle of the column and obtaining three streams, one stream indicated as being withdrawn from the top of the column, one stream indicated as being withdrawn as a side-draw from the side of the column, and one stream indicated as being withdrawn from the bottom of the column. Depending on the conditions used to operate the distillation column and the desired degree of separation, the streams can also be introduced at other feed points and obtained from other withdrawal points.

Referring to FIG. 1, the HCN-containing feed (abbreviated as "HCN" in the Figures), the BD-containing feed (abbreviated as "BD" in the Figures), and the catalyst composition (abbreviated as "cat" in the Figures) are contacted in a reaction zone 10 to produce a reaction mixture 12 comprising 3PN and 2M3BN, wherein the 2M3BN concentration is maintained below about 15 weight percent of the total mass of the reaction mixture. The reaction mixture 12 exits the reaction zone and is introduced into a first distillation column 14. In the first distillation column 14, the reaction mixture 12 is distilled to obtain a first overhead stream 16 comprising BD, a first side-draw stream 18 comprising 3PN, 2M3BN, (Z)-2M2BN, and optionally BD, and a first bottom stream 20 comprising the catalyst composition. As a result of the distillation, the first overhead stream 16 is enriched in BD and depleted in pentenenitriles, including 3PN and 2M3BN, as compared to the reaction mixture. The first side-draw stream 18 is depleted in BD and enriched in pentenenitriles, including 3PN and 2M3BN, as compared to the reaction mixture. The first bottom stream 20 is enriched in the catalyst composition and depleted in BD as compared to the reaction mixture. Both the first overhead stream 16 and the first side-draw stream 18 are depleted in catalyst composition as compared to the reaction mixture.

The first side-draw stream 18 is introduced into a second distillation column 22, in which the first side-draw stream 18 is distilled to obtain a second overhead stream 24 comprising BD, a second side-draw stream 26 comprising 2M3BN, (Z)-2M2BN, and optionally BD, and a second bottom stream 28 comprising 3PN. As a result of the distillation, the second overhead stream 24 is enriched in BD and depleted in pentenenitriles, including 3PN and 2M3BN, as compared to the first side-draw stream 18. The second side-draw stream 26 is depleted in 3PN and enriched in 2M3BN and (Z)-2M2BN, as compared to the first side-draw stream 18. The second bottom stream 28 is enriched in 3PN and depleted in 2M3BN and (Z)-2M2BN, as compared to the first side-draw stream 18.

The second side-draw stream 26 is introduced into a third distillation column 30, in which the second side-draw stream 26 is distilled to obtain a third overhead stream 32 comprising BD, a third side-draw stream 34 comprising (Z)-2M2BN, and a third bottom stream 36 comprising 2M3BN. As a result of the distillation, the third overhead stream 32 is enriched in BD and depleted in pentenenitriles, including 2M3BN and (Z)-2M2BN, as compared to the second side-draw stream 26. The third side-draw stream 34 is depleted in 2M3BN and enriched in (Z)-2M2BN, as compared to the second side-draw stream. The third bottom stream 36 is enriched in 2M3BN and depleted in (Z)-2M2BN, as compared to the second side-draw stream 26.

In describing the process illustrated by FIG. 1, the streams obtained by distillation may also be referred to without specifying their withdrawal points from the distillation columns. Accordingly, the first overhead stream 16 may also be referred to as the first stream 16, the second side-draw stream 18 may also be referred to as the second stream 18, and the third bottom stream 20 may also be referred to as the third stream 20. Similarly, the second overhead stream 24 may also be referred to as the fourth stream 24, the second side-draw stream 26 may also be referred to as the fifth stream 26, and the second bottom stream 28 may also be referred to as the sixth stream 28. Likewise, the third overhead stream 32 may also be referred to as the seventh stream 32, the third side-draw stream 34 may also be referred to as the eighth stream 34, and the third bottom stream 36 may also be referred to as the ninth stream 36.

FIG. 2 schematically illustrates another embodiment of the processes of the invention. In FIG. 2, each apparatus is shown as having a feed point in the middle of the column or condenser and obtaining two streams, one stream indicated as being withdrawn from the top of the apparatus and one stream indicated as being withdrawn from the bottom of the apparatus. Depending on the conditions used to operate the distillation columns and the desired degree of separation, the streams can also be introduced at other feed points and obtained from other withdrawal points. A portion of the liquid stream obtained from each partial condenser may also be returned as reflux to the distillation column from which it is obtained (not shown).

Referring to FIG. 2, the HCN-containing feed, the BD-containing feed, and the catalyst composition are contacted in a reaction zone 10 to produce a reaction mixture 12 comprising 3PN and 2M3BN, wherein the 2M3BN concentration is maintained below about 15 weight percent of the total mass of the reaction mixture. The reaction mixture 12 exits the reaction zone and is introduced into a first distillation column 14. In the first distillation column 14, the reaction mixture 12 is distilled to obtain a combination stream A. The combination stream A is introduced into at least one partial condenser 15 in which a first stream 16 comprising 1,3-butadiene is obtained from stream A as a vapor stream, and a second stream 18 comprising 3PN, 2M3BN, (Z)-2M2BN, and optionally 1,3-butadiene is obtained from stream A as a liquid stream. The first stream 16 is enriched in BD and depleted in pentenenitriles, including 3PN and 2M3BN, as compared to the reaction mixture. The second stream is depleted in BD and enriched in pentenenitriles, including 3PN and 2M3BN, as compared to the reaction mixture. Distillation of the reaction mixture 12 in the first distillation column 14 also obtains an additional stream, the third stream 20, which comprises the catalyst composition. The third stream 20 is enriched in the catalyst composition and depleted in BD as compared to the reaction mixture. Both the first stream 16 and the second stream 18 are depleted in catalyst composition as compared to the reaction mixture.

The second stream 18 is introduced into a second distillation column 22, in which the second stream 18 is distilled to obtain a combination stream B. The combination stream B is introduced into at least one partial condenser 17, in which a fourth stream 24 comprising BD is obtained from stream B as a vapor stream, and a fifth stream 26 comprising 2M3BN, (Z)-2M2BN, and optionally BD is obtained from stream B as a liquid stream. The fourth stream 24 is enriched in BD and depleted in pentenenitriles, including 3PN and 2M3BN, as compared to the second stream 18. The fifth stream 26 is depleted in 3PN and enriched in 2M3BN and (Z)-2M2BN, as compared to the second stream 18. Distillation of the second stream 18 in the second distillation column 22 also obtains an additional stream, the sixth stream 28, which comprises 3PN. The sixth stream 28 is enriched in 3PN and depleted in 2M3BN and (Z)-2M2BN as compared to the second stream 18.

The fifth stream 26 is introduced into a third distillation column 30 in which the fifth stream 26 is distilled to obtain a combination stream C. The combination stream C is introduced into at least one partial condenser 19, in which a seventh stream 32 comprising BD is obtained from stream C as a vapor stream, and an eighth stream comprising (Z)-2M2BN is obtained from stream C as a liquid stream. The seventh stream 32 is enriched in BD and depleted in pentenenitriles including 2M3BN and (Z)-2M2BN, as compared to the fifth stream 26. Distillation of the fifth stream 26 in the third distillation column 30 also obtains an additional stream, the ninth stream 36, which comprises 2M3BN. The ninth stream 36 is enriched in 2M3BN and depleted in (Z)-2M2BN and compared to the fifth stream 26.

In another embodiment of the process, at least a portion of the ninth stream comprising 2M3BN is returned to the reaction zone in which BD hydrocyanation and 2M3BN isomerization occurs. FIG. 3 schematically illustrates one embodiment of the process in which 2M3BN, indicated as stream 36, is returned to the reaction zone 10. Returning 2M3BN to the reaction zone permits conversion of at least a portion of it to 3PN, which can be hydrocyanated to produce ADN, and increases the overall yield based on BD. Potential advantages of such a process can include the elimination of investment and of the associated variable and fixed costs for operating an additional 2M3BN isomerization reaction vessel, distillation columns, and the associated pumps, heat exchangers, piping, and control instrumentation. Alternatively, a feed comprising 2M3BN can be produced by a different process or prepared in a separate manufacturing facility and introduced into the reaction zone, with or without the return of at least a portion of the ninth stream comprising 2M3BN to the reaction zone.

In another embodiment of the process, at least a portion of the first stream, the fourth stream, the seventh stream, or combinations thereof is returned to the reaction zone. These streams comprise BD, and returning unreacted BD to the reaction zone for hydrocyanation can improve the overall yield of the 3PN process, based on BD. The streams comprising BD may be combined partially or totally before return to the reaction zone, or they may remain uncombined. The streams may be returned as vapor streams, or they may be at least partially condensed, and the vapor and/or liquid phases returned to the reaction zone. FIG. 3 schematically illustrates one embodiment of the process in which the first stream, shown as stream 16, the fourth stream, shown as stream 24, and the seventh stream, shown as stream 32, are individually returned to the reaction zone 10. Alternatively, only one of the streams, or a combination of two of them, can be returned at least in part to the reaction zone. As shown in FIG. 3, in one embodiment of the processes of the invention both unreacted BD and 2M3BN can be returned to the reaction zone. Alternatively, unreacted BD or 2M3BN can be returned independently to the reaction zone.

The first, fourth, and seventh streams comprise BD, and each may further comprise butene if the BD-containing feed to the reaction zone additionally comprises butene. As disclosed in U.S. Pat. No. 4,434,316, butene generally does not react under conditions where BD is hydrocyanated, which provides a process for separating alkenes, e.g. butene from mixtures of alkenes and alkadienes, e.g. BD wherein the separation is achieved by preferentially reacting HCN with the diene by contacting the mixture with HCN under hydrocyanation conditions, preferably in the presence of a zerovalent nickel catalyst. In the process of the invention, butene exits the reaction zone and at least a portion of the butene enters the refining process with the BD. When at least a portion of the BD in the first stream, the fourth stream, the seventh stream, or combinations thereof, is returned to the reaction zone, at least a portion of the unreacted butene is also returned to the reaction zone, and the inert butene builds up in the recycle loop unless a purge is taken. To this end, at least a portion of the first stream, the fourth stream, the seventh stream, or combinations thereof can be withdrawn to purge at least a portion of the butene prior to returning the streams comprising the unreacted BD to the reaction zone.

The rate at which butene accumulates in the recycle loop is related to the amount of butene present in the BD entering the process. If the amount of butene in the BD feed is low, butene will accumulate slowly in the recycle loop. With higher amounts of butene in the feed BD, butene will accumulate more rapidly in the recycle loop. A butene purge can be taken as a liquid or a vapor stream when the total butene content of at least one of the first stream, the fourth stream, the seventh stream, or combinations thereof is significant enough that operational efficiency will be improved by purging at least a portion of the butene, for example when the total butene content of at least one of the first stream, the fourth stream, the seventh stream, or combinations thereof is greater than about 20 percent by weight, or for example greater than about 30 percent by weight, or for example greater than about 40 percent by weight, or for example greater than about 50 percent by weight, or for example greater than about 60 percent by weight of the total mass of the stream. When the butene purge is taken as a vapor, the purge rate can be controlled by adding an inert gas or by adjusting the recovery conditions, for example by increasing the condenser temperature or decreasing the pressure. Allowing the butene to accumulate in the BD recycle loop can lessen the BD costs in purging the butene from the process. The butene purge stream may be returned to a BD plant, for example, to recover the BD and butene value and to reduce emissions.

In another embodiment of the process, at least a portion of the ninth stream comprising 2M3BN is contacted with at least a portion of the first stream comprising BD to produce a recycle stream comprising 2M3BN and BD, and the recycle stream is returned to the reaction zone. For improved performance, the 2M3BN can be chilled before being contacted with the first stream comprising BD. If desired, to improve recovery the first stream comprising BD can be compressed to above atmospheric pressure. The recycle stream is returned as a liquid stream to the reaction zone. The ninth stream and the first stream can be contacted in any suitable equipment known to one skilled in the art, for example in a scrubber. The contacting can be performed in one or more vessels.

FIG. 4 schematically illustrates one embodiment of the processes of the invention which includes contacting 2M3BN, indicated as stream 36, with unreacted BD, indicated as stream 16, in apparatus 38 to produce a recycle stream, indicated in FIG. 4 as stream 40, which is returned to the reaction zone 10.

In another embodiment, at least a portion of the third stream comprising the catalyst composition is returned to the reaction zone. A portion of the third stream comprising the catalyst composition may be purged before the stream is returned to the reaction zone to prevent build-up of high boiling impurities. Examples of high boiling impurities include $C_9$ mononitriles and 4-vinyl-1-cyclohexene.

The sixth stream comprising 3PN may be hydrocyanated to produce a dinitrile product comprising ADN. The sixth stream may be used in this manner without further refinement. The hydrocyanation is performed with an appropriate catalyst, for example a zero-valent nickel catalyst composition comprising a phosphorus-containing ligand, and at least one Lewis acid promoter. Reaction conditions for hydrocyanation of mixtures comprising 3PN in the presence of a Lewis acid promoter are disclosed, for example, in U.S. Pat. Nos. 5,723,641; 5,959,135; and 6,127,567, all of which are incorporated herein by reference.

Most commercially available BD contains 4-tert-butylcatechol (TBC) in amounts ranging from 10-300 ppm. TBC is added to the BD as an inhibitor against peroxidation and polymer formation, which are undesirable reactions that can lead to vessel rupture and explosion. TBC is considered undesirable in hydrocyanation reactions, for example with catalyst compositions comprising bidentate phosphite ligands, as disclosed in published application EP 1344770, because TBC can react with bidentate phosphite ligands to produce new monophosphite species, which in turn can produce new nickel complexes which are less active or inactive for hydrocyanation than the catalyst derived from only the bidentate phosphite ligand.

Water may also be present in commercially available BD. Water is undesirable in hydrocyanation processes as it may react with the phosphorus-containing ligands to produce hydrolysis products which are less active or inactive for the desired hydrocyanation and isomerization reactions. The ligand hydrolysis products may also promote undesired side reactions.

Prior to its use in hydrocyanation, BD may be purified to remove impurities such as TBC and water. TBC may be removed from BD by a variety of techniques, for example by distillation or by passing the liquid BD over an absorbent bed such as alumina. Distillation can also be used to remove other impurities, for example 4-vinyl-1-cyclohexene, from BD. Water may be removed from BD by a variety of techniques, for example by passing liquid BD over molecular sieves having a pore size smaller than 10 Angstrom units or by contacting it with alumina.

FIG. 5 indicates schematically one embodiment of a process for the purification of BD before it is fed to the reaction zone. In FIG. 5, BD containing TBC and water is first distilled in distillation column 2 to provide a bottom stream 1 comprising TBC and a stream 4 comprising BD which is substantially free of TBC. Stream 4 is then passed over molecular sieves in apparatus 6, which may be for example a column or bed, to provide stream 8 comprising BD which is substantially free of water. Stream 8 is then fed to the reaction zone, along with HCN and the catalyst composition, to produce a reaction mixture 12 comprising 3PN and 2M3BN.

Optionally, an additional stream (not shown in FIG. 5) comprising a high boiling material, for example a dinitrile such as 2-methylglutaronitrile, may be fed to the distillation column in addition to the BD. In this case, the bottom stream 1 obtained by distillation comprises TBC and the higher boiling material. The higher boiling material functions as a carrier for the TBC and facilitates its handling.

As compared to a 3PN production process in which BD hydrocyanation and 2M3BN isomerization are performed in separate reaction zones under reaction conditions optimized independently for BD hydrocyanation to 3PN or for 2M3BN isomerization to 3PN, a process in which BD hydrocyanation and 2M3BN isomerization occur concurrently in the same reaction zone, and in which the 2M3BN concentration in the reaction mixture is maintained below about 15 weight percent of the total mass of the reaction mixture, can avoid the requirement for a separate reactor dedicated to 2M3BN isomerization. This also eliminates a separate catalyst recycle loop associated with a separate 2M3BN isomerization reactor. Furthermore, when the molar ratio of the HCN in the feed to the BD in the feed is in the range of about 0.90:1.00 to about 1.04:1.00 and the residence time in the reaction zone is sufficient to convert about 95% or more of the HCN, the amount of unreacted BD in the reaction mixture is sufficiently low that a separate distillation column dedicated to separating unreacted BD from the reaction mixture is unnecessary, and unreacted BD can be separated from the reaction mixture by the distillation sequence described above. The integration of a pentenenitrile refining process with a 3PN process, in which BD hydrocyanation and 2M3BN isomerization occur in the same reaction zone to provide a reaction mixture wherein the 2M3BN concentration is maintained below about 15 weight percent of the total mass of the reaction mixture, would be advantageous for at least these reasons.

Experimental Section

Examples 1-4 were performed using a catalyst composition wherein the multidentate P-containing ligand was a bidentate P-containing ligand, referred to as "Phosphite A" in the chemical formula for the nickel source below. The multidentate P-containing ligand of the Examples is represented by Formula XXXIII wherein $R^{41}$ is isopropyl; $R^{42}$, $R^{46}$, and $R^{48}$ are H; and $R^{43}$, $R^{44}$, $R^{45}$, and $R^{47}$ are methyl. The nickel source charged to the autoclave comprised the compound (Phosphite A)Ni(crotyl)CN dissolved in a nitrile solvent mixture. This compound is in equilibrium with the zero-valent nickel complex (Phosphite A)Ni(PN) wherein PN can be 3PN, 2M3BN, or other pentenenitriles in the nitrile solvent mixture. "Crotyl" represents a butenyl group having the empirical formula $C_4H_7$.

The multidentate P-containing ligand, Phosphite A, of the Examples may be prepared by any suitable synthetic means known in the art. For example, 3,3'-diisopropyl-5,5',6,6'-tetramethyl-2,2'-biphenol can be prepared by the procedure disclosed in United States Published Patent Application No. 2003/0100802, which is incorporated herein by reference, in which 4-methylthymol can undergo oxidative coupling to the substituted biphenol in the presence of a copper chlorohydroxide-TMEDA complex (TMEDA is N,N,N',N'-tetramethylethylenediamine) and air.

The phosphorochloridite of 2,4-xylenol, $(C_8H_9O)_2PCl$, can be prepared, for example, by the procedure disclosed in United States Published Patent Application No. 2004/0106815, which is incorporated herein by reference. To form this phosphorochloridite selectively, anhydrous triethylamine and 2,4-xylenol can be added separately and concurrently in a controlled manner to $PCl_3$ dissolved in an appropriate solvent under temperature-controlled conditions.

The reaction of the phosphorochloridite with the 3,3'-diisopropyl-5,5',6,6'-tetramethyl-2,2'-biphenol to form the desired ligand, Phosphite A, can be performed, for example, according to the method disclosed in U.S. Pat. No. 6,069,267, which is hereby incorporated by reference. The phosphorochloridite can be reacted with 3,3'-diisopropyl-5,5',6,6'-tetramethyl-2,2'-biphenol in the presence of an organic base to form Phosphite A, which can be isolated according to techniques well known in the art, as also described in U.S. Pat. No. 6,069,267. The monodentate phosphite impurities in Phosphite A prepared by this method would have the following structures.

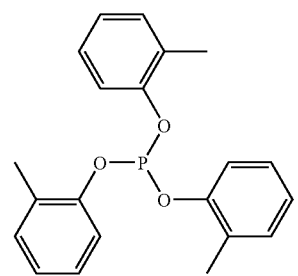

-continued

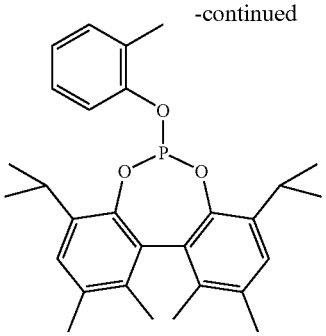

For each Example, the (Phosphite A)Ni(crotyl)CN compound was prepared as follows. In a nitrogen atmosphere, the Phosphite A, represented by Formula XXXIII wherein $R^{41}$ is isopropyl; $R^{42}$, $R^{46}$, and $R^{48}$ are H; and $R^{43}$, $R^{44}$ $R^{45}$, and $R^{47}$ are methyl, and Ni(COD)$_2$(COD is 1,5-cyclooctadiene) were combined in a molar ratio of 1:1 in a flask. Trans-3-pentenenitrile (95 wt %, Aldrich), which had been previously dried over molecular sieves and degassed with nitrogen, was added to the same flask (about 200 mL for 10 g of Phosphite A) and the mixture was stirred until an orange homogeneous solution formed. All volatiles were removed under vacuum at ambient temperature to yield an orange powder. The powder was triturated with anhydrous acetonitrile to remove excess pentenenitriles and other impurities, and then all volatiles were again removed under vacuum to produce (Phosphite A)Ni (crotyl)CN as an orange solid.

Trans-3-pentenenitrile (95 wt %) produced from BD hydrocyanation, 2M3BN isomerization, and pentenenitrile hydrocyanation processes may be obtained commercially from the Sigma-Aldrich Chemical Company. This material contains trace amounts of 2M3BN also prepared from a BD hydrocyanation and/or 2M3BN isomerization process.

The purity of the BD feed was greater than 99%. Freshly prepared anhydrous, uninhibited, liquid HCN was utilized in all Examples.

Embodiments falling within the scope of the present invention may be further understood in view of the following non-limiting examples.

EXAMPLES

Example 1

The reaction was carried out in a 100 mL autoclave fitted with a magnetically driven stirrer and dip legs for the addition of feeds. The reactor was operated liquid full, which resulted in a working volume of 118 mL. The reaction temperature was maintained at 120° C. by means of a combination of electrical heating on the outside and passing coolant through an internal coil. Pressure in the reactor was controlled by a manual back-pressure regulator at 130 psia (896 kPa). The exit tube continuously fed a flash-distillation column, which operated under reduced pressure (100 torr; 13.3 kPa) to separate reaction products from the catalyst.

A catalyst composition solution comprised of (Phosphite A)Ni(crotyl)CN (2.5 wt%), 1.6 wt% Phosphite A, and 1.2 wt% Phosphite A oxides, 3PN (82 wt %), 2PN (0.9 wt %), 4PN (1.2 wt %), 2M3BN (1.4 wt %), 2-methyl-2-butenenitriles (2M2BN, 0.7 wt %), dimethylsuccinonitrile (1.0 wt %), MGN (3.5 wt %), and ADN (2.4 wt %), was fed continuously and concurrently with BD and HCN to the autoclave such that the molar ratio of Ni:HCN:BD fed was about 0.00046:0.963: 1.0 and the total flow rates were such that the residence time in the reactor was about 3.4 hours. Flows were maintained for 24 hours in order to approach a steady state condition. Samples were periodically drawn from the line exiting the reactor and analyzed by both high-pressure liquid chromatography (HPLC) for catalyst and by gas chromatography (GC) for nitrile products and byproducts. The 2M3BN was analyzed at 6.6 wt % of the reaction mixture. 92.9% of the BD and 96.5% of the HCN fed to the autoclave was converted into useful products comprised of 2PN, 3PN, 4PN, and 2M3BN. Of the total moles of BD converted, the selectivity to these useful products was 96.7%.

Example 2

The reaction was carried out in a 1 liter autoclave fitted with a magnetically driven stirrer and dip legs for the addition of feeds and removal of product. The product removal dip leg was adjusted to provide a working volume of 750 mL. The reaction temperature was maintained at 110° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN: BD fed was about 0.00055:0.946:1.0 and the total flow rates were such that the residence time in the reactor was about 7.3 hours. Flows were maintained for 40 hours in order to approach a steady state condition. Samples were periodically drawn from the line exiting the reactor and analyzed by both HPLC for catalyst and by GC for nitrile products and byproducts. The 2M3BN was analyzed at 6.6 wt % of the reaction mixture. 91.1% of the BD and 96.3% of the HCN fed to the autoclave was converted into useful products comprised of 2PN, 3PN, 4PN, and 2M3BN. Of the total moles of BD converted, the selectivity to these useful products was 96.1%.

Example 3

The reaction was carried out in a 1 liter autoclave fitted with a magnetically driven stirrer and dip legs for the addition of feeds and extraction of product. The product removal dip leg was adjusted to provide a working volume of 750 mL. The reaction temperature was maintained at 120° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN: BD fed was about 0.00025:0.948:1.0 and the total flow rates were such that the residence time in the reactor was about 8.2 hours. Flows were maintained for 40 hours in order to approach a steady state condition. Samples were periodically drawn from the line exiting the reactor and analyzed by both HPLC for catalyst and by GC for nitrile products and byproducts. The 2M3BN was analyzed at 10.3 wt % of the reaction mixture. 90.9% of the BD and 96.9% of the HCN fed to the autoclave was converted into useful products comprised of 2PN, 3PN, 4PN, and 2M3BN. Of the total moles of BD converted, the selectivity to these useful products was 96.5%.

Example 4

The reaction was carried out in a 1 liter autoclave fitted with a magnetically driven stirrer and dip legs for the addition of feeds and extraction of product. The product removal dip leg was adjusted to provide a working volume of 750 mL. The reaction temperature was maintained at 130° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00035:0.925:1.0 and the total flow rates were such that the residence time in the reactor was about 2.0 hours. Flows were maintained for 12 hours in order to approach a steady state condition. Samples were periodically drawn from the line exiting the reactor and analyzed by both HPLC for catalyst and by GC for nitrile products and byproducts. The 2M3BN was analyzed at 12.4 wt % of the reaction mixture. 89.1% of the BD and 96.3% of the HCN fed to the autoclave was converted into useful products comprised of 2PN, 3PN, 4PN, and 2M3BN. Of the total moles of BD converted, the selectivity to these useful products was 96.7%.

Example 5

Example 5 demonstrates the integrated, continuous process of the invention operating at steady state. This Example uses a catalyst composition wherein the multidentate P-containing ligand is the bidentate P-containing ligand referred to as "Phosphite A." Phosphite A is prepared as described in the section above and is obtained as a ligand mixture comprising Phosphite A and the monodentate phosphites having the following structures:

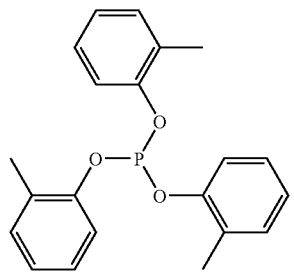

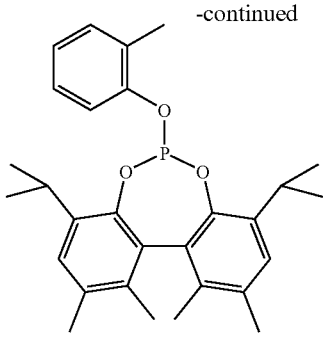

A portion of the catalyst composition is obtained as follows. Phosphite A, anhydrous NiCl$_2$, zinc powder, and 3-pentenenitrile are contacted according to the method disclosed in U.S. Pat. No. 6,893,996, which is incorporated herein by reference, to prepare a fresh catalyst composition. The fresh catalyst composition is treated with ammonia, as disclosed in U.S. Pat. No. 3,766,241 which is incorporated herein by reference, and filtered. The treated fresh catalyst composition, in addition to the catalyst composition of the third stream (see below), is used in the hydrocyanation of 1,3-butadiene (BD).

After undergoing distillation to remove 4-tert-butylcatechol and 4-vinyl-1-cyclohexene and drying to remove water, BD containing about 0.30 wt % butene is contacted in a continuous manner with HCN in a 1.02:1 BD:HCN molar ratio in the presence of a catalyst composition comprising Phosphite A and a zero-valent nickel [about 300 ppm zero-valent nickel, Ni(0)] in a 2:1 Phosphite A:Ni molar ratio in a reaction zone consisting of a stainless steel, draft-tube, back-mixed reactor with a holdup time of about 3 hours. The reaction zone is maintained at 120° C. to achieve about 96% conversion of BD and to produce a reaction mixture containing about 2.6 wt % BD, about 3.3 wt % butene, about 0.01 wt % HCN, about 1.9 wt % (Z)-2M2BN, about 6.3 wt % 2M3BN, and about 76.1 wt % total of 3PN and 4PN.

The reaction mixture is introduced into the bottom of a distillation column having one theoretical stage of packing above the feed location and continuously distilled. The column head pressure is about 5.8 psia (about 0.4 bar) and the column bottom temperature is 120° C. The first stream obtained is a vapor stream withdrawn from the top of the partial condenser and contains about 40.5 wt % BD, about 45.9 wt % butene, about 2.2 wt % 2M3BN, and about 8.3 wt % total of 3PN and 4PN. The second stream obtained is withdrawn from the reflux back to the column and contains about 8.5 wt % 2M3BN, about 2.1 wt % (Z)-2M2BN, about 79.2 wt % total of 3PN and 4PN, about 1.8 wt % BD, and about 2.4 wt % butene. The column base is heated by circulating the bottoms material through an external steam-heated exchanger. The third stream is obtained by withdrawing a portion from the circulating bottoms material and contains about 2.6 wt % 2M3BN, about 52.4 wt % total 3PN and 4PN, about 10 wt % Phosphite A, and about 0.3 wt % Ni(0).

The second stream is introduced into a distillation column such that about 15 theoretical stages are above and about 45 theoretical stages are below the feed location and continuously distilled. The column head pressure is about 16.4 psia (about 1.1 bar) and the column head temperature is 120° C. The fourth stream obtained is a vapor stream withdrawn from the top of the partial condenser and contains about 40.6 wt % BD, about 49.3 wt % butene, about 5.3 wt % 2M3BN, and about 0.2 wt % total of 3PN and 4PN. The fifth stream obtained is withdrawn from the reflux back to the column and contains about 51.7 wt % 2M3BN, about 12.7 wt % (Z)-2M2BN, about 5.2 wt % BD, about 8.0 wt % butene, and about 5.0 wt % total 3PN and 4PN. The sixth stream obtained is withdrawn from the base of the column and contains about 96.1 wt % total 3PN and 4PN and about 0.1 wt % 2M3BN.

The fifth stream is introduced near the base of a distillation column having 40 theoretical stages and continuously distilled. The column head pressure is about 15.5 psia (about 1.07 bar) and the column head temperature is 108° C. The seventh stream obtained is a vapor stream withdrawn from the top of the partial condenser and contains about 34.4 wt % BD, about 50.8 wt % butene, and about 3.6 wt % 2M3BN. The eighth stream obtained is withdrawn from the reflux back to the column and contains about 20.6 wt % (Z)-2M2BN, about 29.5 wt % 2M3BN, about 33.5 wt % 4-vinyl-1-cyclohexene, about 4.6 wt % BD, and about 9.4 wt % butene. The ninth stream obtained is withdrawn from the base of the column and contains about 62.9 wt % 2M3BN, about 13.4 wt % (Z)-2M2BN, and about 6.5 wt % total 3PN and 4PN.

The fourth and seventh streams are combined and introduced into a condenser at −12° C. and 1.05 bar. The vapor stream exiting the condenser contains about 40.8 wt % BD and about 47.4 wt % butene. A portion of this stream is withdrawn and purged from the 3PN manufacturing process while the remainder is returned to the reaction zone. In this way at least a portion of the butene in the fourth and seventh streams is purged, and at least a portion of the 1,3-butadiene in the fourth and seventh streams is returned to the reaction zone.

The first stream and the ninth stream are introduced into a scrubber maintained at −7° C. The liquid stream obtained, containing about 5.6 wt % BD, about 6.4 wt % butene, and about 54.7 wt % 2M3BN, is returned to the reaction zone.

At least a portion of the sixth stream is hydrocyanated to produce a dinitrile product comprising adiponitrile.

At least a portion of the third stream is returned to the reaction zone to be used in the hydrocyanation of BD.

At least a portion of the third stream is introduced into a liquid-liquid extraction process to recover at least a portion of the catalyst composition and at least a portion is returned to the reaction zone.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. An integrated, continuous process for the production of 3-pentenenitrile, the refining of 3-pentenenitrile, and the refining of 2-methyl-3-butenenitrile, the process comprising:
    (a) contacting, in a reaction zone, a hydrogen cyanide-containing feed, a 1,3-butadiene-containing feed, and a catalyst composition, wherein the catalyst composition comprises a zero-valent nickel and at least one bidentate phosphorus-containing ligand selected from the group consisting of a phosphite, a phosphonite, a phosphinite, a phosphine, a mixed phosphorus-containing ligand, and combinations thereof;
    (b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture;
    (c) distilling the reaction mixture to obtain a first stream comprising 1,3-butadiene, a second stream comprising 3-pentenenitrile, 2-methyl-3-butenenitrile, (Z)-2-methyl-2-butenenitrile, and optionally 1,3-butadiene, and a third stream comprising the catalyst composition;
    (d) distilling the second stream to obtain a fourth stream comprising 1,3-butadiene, a fifth stream comprising 2-methyl-3-butenenitrile, (Z)-2-methyl-2-butenenitrile, and optionally 1,3-butadiene, and a sixth stream comprising 3-pentenenitrile; and
    (e) distilling the fifth stream to obtain a seventh stream comprising 1,3-butadiene, an eighth stream comprising (Z)-2-methyl-2-butenenitrile, and a ninth stream comprising 2-methyl-3-butenenitrile.

2. The process of claim 1, wherein at least one distilling process separately obtains a combination stream and an additional stream; wherein
    the distilling process is selected from the group consisting of (c) distilling the reaction mixture, (d) distilling the second stream, (e) distilling the fifth stream, and combinations thereof;
    the combination stream is introduced into at least one partial condenser to obtain a vapor stream and a liquid stream;
    when the distilling process is (c) distilling the reaction mixture, the combination stream is stream A, the vapor stream obtained from stream A is the first stream comprising 1,3-butadiene, the liquid stream obtained from stream A is the second stream comprising 3-pentenenitrile, 2-methyl-3-butenenitrile, (Z)-2-methyl-2-butenenitrile, and optionally 1,3-butadiene, and the additional stream is the third stream;
    when the distilling process is (d) distilling the second stream, the combination stream is stream B, the vapor stream obtained from stream B is the fourth stream comprising 1,3-butadiene, the liquid stream obtained from stream B is the fifth stream comprising 2-methyl-3-butenenitrile, (Z)-2-methyl-2-butenenitrile, and optionally 1,3-butadiene, and the additional stream is the sixth stream; and
    when the distilling process is (e) distilling the fifth stream, the combination stream is stream C, the vapor stream obtained from stream C is the seventh stream comprising 1,3-butadiene, the liquid stream obtained from stream C is the eighth stream comprising (Z)-2-methyl-2-butenenitrile, and the additional stream is the ninth stream.

3. The process of claim 1, wherein (c) distilling the reaction mixture obtains a stream A and the third stream; and stream A is introduced into at least one partial condenser to obtain the first stream as a vapor stream comprising 1,3-butadiene and the second stream as a liquid stream comprising 3-pentenenitrile, 2-methyl-3-butenenitrile, (Z)-2-methyl-2-butenenitrile, and optionally 1,3-butadiene.

4. The process of claim 1, wherein (d) distilling the second stream obtains a stream B and the sixth stream; and stream B is introduced into at least one partial condenser to obtain the fourth stream as a vapor stream comprising 1,3-butadiene and the fifth stream as a liquid stream comprising 2-methyl-3-butenenitrile, (Z)-2-methyl-2-butenenitrile, and optionally 1,3-butadiene.

5. The process of claim 1, wherein (e) distilling the fifth stream obtains a stream C and the ninth stream; and stream C is introduced into at least one partial condenser to obtain the seventh stream as a vapor stream comprising 1,3-butadiene and the eighth stream as a liquid stream comprising (Z)-2-methyl-2-butenenitrile.

6. The process of claim 1, wherein
distilling the reaction mixture obtains a stream A and the third stream;
stream A is introduced into at least one partial condenser to obtain the first stream as a vapor stream comprising 1,3-butadiene and the second stream as a liquid stream comprising 3-pentenenitrile, 2-methyl-3-butenenitrile, (Z)-2-methyl-2-butenenitrile, and optionally 1,3-butadiene;
distilling the second stream obtains a stream B and the sixth stream;
stream B is introduced into at least one partial condenser to obtain the fourth stream as a vapor stream comprising 1,3-butadiene and the fifth stream as a liquid stream comprising 2-methyl-3-butenenitrile, (Z)-2-methyl-2-butenenitrile, and optionally 1,3-butadiene;
distilling the fifth stream obtains a stream C and the ninth stream; and
stream C is introduced into at least one partial condenser to obtain the seventh stream as a vapor stream comprising 1,3-butadiene and the eighth stream as a liquid stream comprising (Z)-2-methyl-2-butenenitrile.

7. The process of claim 1 or claim 2, wherein at least a portion of the ninth stream comprising 2-methyl-3-butenenitrile is returned to the reaction zone.

8. The process of claim 1 or claim 2, wherein at least a portion of the first stream, the fourth stream, the seventh stream, or combinations thereof is returned to the reaction zone.

9. The process of claim 1 or claim 2, wherein at least one of the first stream, the fourth stream, or the seventh stream further comprises butene, and at least a portion of the first stream, the fourth stream, the seventh stream, or combinations thereof is withdrawn to purge at least a portion of the butene prior to returning the stream to the reaction zone.

10. The process of claim 1 or claim 2, wherein the total butene content of at least one of the first stream, the fourth stream, or the seventh stream is greater than about 20 percent by weight.

11. The process of claim 1 or claim 2, wherein at least a portion of the ninth stream comprising 2-methyl-3-butenenitrile is contacted with at least a portion of the first stream comprising 1,3-butadiene to produce a recycle stream comprising 2-methyl-3-butenenitrile and 1,3-butadiene, and the recycle stream is returned to the reaction zone.

12. The process of claim 1 or claim 2, wherein at least a portion of the third stream comprising the catalyst composition is returned to the reaction zone.

13. The process of claim 1 or claim 2, wherein at least a portion of the sixth stream comprising 3-pentenenitrile is hydrocyanated to produce a dinitrile product comprising adiponitrile.

14. The process of claim 1 or claim 2, wherein the 1,3-butadiene-containing feed comprises 1,3-butadiene which has been distilled to remove an impurity selected from the group consisting of 4-tert-butylcatechol, 4-vinyl-1-cyclohexene, and combinations thereof.

15. The process of claim 1 or claim 2, wherein the reaction mixture is distilled in at least one distillation column at less than one atmosphere pressure and with a base temperature of about 120° C. or less.

16. The process of claim 1 or claim 2, wherein the second stream is distilled in at least one distillation column at or above one atmosphere pressure and wherein the sixth stream contains less than about 1.0 percent by weight 2-methyl-3-butenenitrile.

17. The process of claim 1 or claim 2, wherein the fifth stream is distilled in at least one distillation column and wherein the fifth stream is introduced to the rectifying section of the column.

18. The process of claim 1 or claim 2, wherein the temperature is maintained within a range of about 80° C. to about 140° C.

19. The process of claim 1 or claim 2, wherein the molar ratio of the hydrogen cyanide in the feed to the 1,3-butadiene in the feed is in the range of about 0.90:1.00 to about 1.04:1.00, and the molar ratio of the zero-valent nickel in the feed to the 1,3-butadiene in the feed is in the range of about 0.00005:1.00 to about 0.0050:1.00.

20. The process of claim 1 or claim 2, wherein the bidentate phosphorus-containing ligand is a phosphite ligand selected from a member of the group represented by Formula XXXIII and Formula XXXIV:

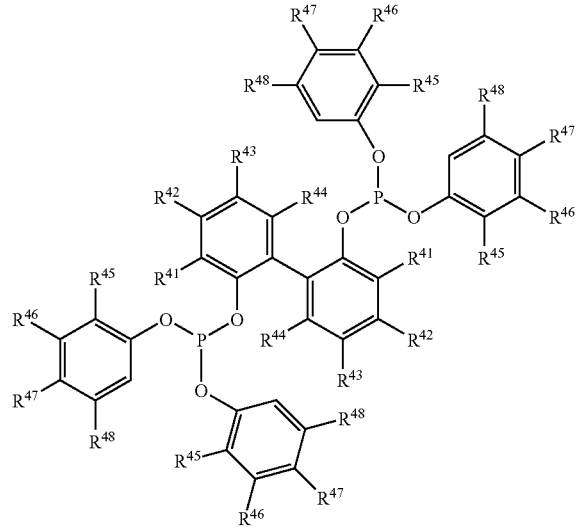

Formula XXXIII

Formula XXXIV

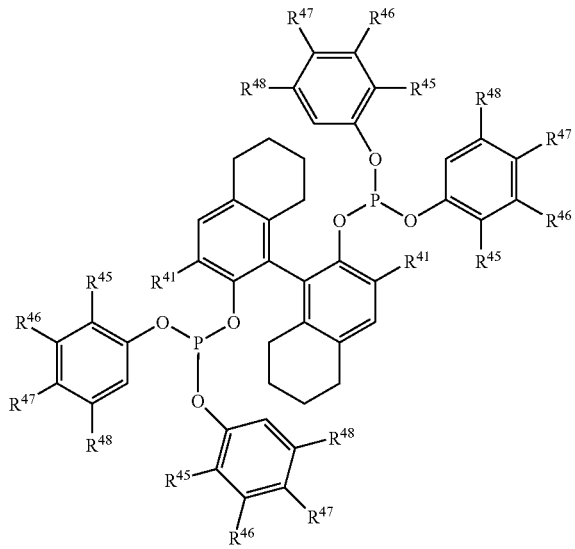

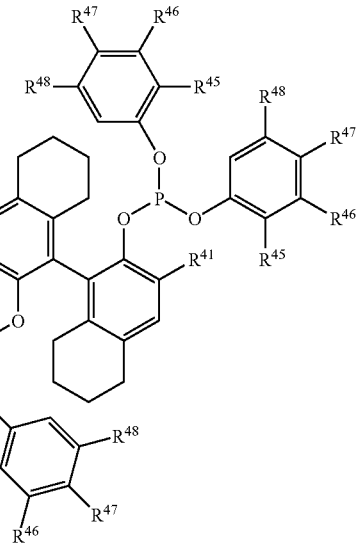

wherein $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl.

21. The process of claim 1 or claim 2 or claim 20, wherein the catalyst composition further comprises at least one monodentate phosphite ligand.

22. An integrated, continuous process for the production of 3-pentenenitrile, the refining of 3-pentenenitrile, and the refining of 2-methyl-3-butenenitrile, the process comprising:
 (a) contacting, in a reaction zone, a hydrogen cyanide-containing feed, a 1,3-butadiene-containing feed, and a catalyst composition, wherein the catalyst composition comprises a zero-valent nickel and at least one bidentate phosphite ligand selected from a member of the group represented by Formulas XXXIII and XXXIV:

Formula XXXIII

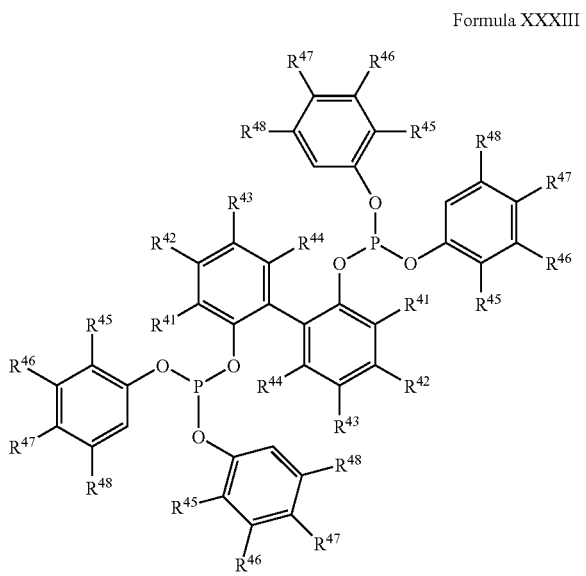

wherein $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl;
 (b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture;
 (c) distilling the reaction mixture to obtain a first overhead stream comprising 1,3-butadiene, a first side-draw stream comprising 3-pentenenitrile, 2-methyl-3-butenenitrile, (Z)-2-methyl-2-butenenitrile, and optionally 1,3-butadiene, and a first bottom stream comprising the catalyst composition;
 (d) distilling the first side-draw stream to obtain a second overhead stream comprising 1,3-butadiene, a second side-draw stream comprising 2-methyl-3-butenenitrile, (Z)-2-methyl-2-butenenitrile, and optionally 1,3-butadiene, and a second bottom stream comprising 3-pentenenitrile;
 (e) distilling the second side-draw stream to obtain a third overhead stream comprising 1,3-butadiene, a third side-draw stream comprising (Z)-2-methyl-2-butenenitrile, and a third bottom stream comprising 2-methyl-3-butenenitrile;
 (f) returning at least a portion of the first overhead stream, the second overhead stream, the third overhead stream, or combinations thereof to the reaction zone; and
 (g) returning at least a portion of the third bottom stream to the reaction zone.

23. The process of claim 22, wherein the catalyst composition further comprises at least one monodentate phosphite ligand.

* * * * *